(12) United States Patent
Kuechler et al.

(10) Patent No.: US 7,288,692 B2
(45) Date of Patent: Oct. 30, 2007

(54) PROCESS FOR PRODUCING OLEFINS

(75) Inventors: Keith H. Kuechler, Friendswood, TX (US); Jeffrey L. Brinen, League City, TX (US); Philip A. Ruziska, Kingwood, TX (US)

(73) Assignee: ExxonMobil Chemcial Patents Inc., Houston, TX (US)

( * ) Notice: Subject to any disclaimer, the term of this patent is extended or adjusted under 35 U.S.C. 154(b) by 458 days.

(21) Appl. No.: 10/891,726

(22) Filed: Jul. 14, 2004

(65) Prior Publication Data
US 2006/0014990 A1    Jan. 19, 2006

(51) Int. Cl.
*C07C 7/00*    (2006.01)
*C07C 1/00*    (2006.01)

(52) U.S. Cl. ............ 585/809; 585/802; 585/833; 585/638; 585/639; 585/640

(58) Field of Classification Search ............ 585/640, 585/809, 802, 638, 639
See application file for complete search history.

(56) References Cited

U.S. PATENT DOCUMENTS

| | | | |
|---|---|---|---|
| 4,929,780 A * | 5/1990 | Wright et al. | 585/303 |
| 6,121,504 A | 9/2000 | Kuechler et al. | 585/640 |
| 6,303,841 B1 | 10/2001 | Senetar et al. | 585/639 |
| 6,403,854 B1 | 6/2002 | Miller et al. | 585/638 |
| 6,459,009 B1 | 10/2002 | Miller et al. | 585/809 |
| 2002/0007101 A1 | 1/2002 | Senetar et al. | 585/809 |
| 2003/0130555 A1 | 7/2003 | Cheng et al. | 585/804 |

FOREIGN PATENT DOCUMENTS

WO    WO 03/033438    4/2003

OTHER PUBLICATIONS

U.S. Appl. No. 10/720,505, filed Nov. 24, 2003 (Inventors—Keith Kuechler, Jeffrey L. Brinen, James Lattner, and Alan S. Gawlik), entitled "Recycling Oxygenate-Rich Streams In Oxygenate-To-Olefin Processes".
U.S. Appl. No. 10/871,394, filed Jun. 18, 2004 (Inventors—Keith Kuechler, Jeffrey L. Brinen, and Philip Andrew Ruziska), entitled "Process For Producing Olefins".
U.S. Patent Application Serial No. Awaited filed Jul. 1, 2004 (Inventors—Keith Kuechler, Jeffrey L. Brinen, and Philip Andrew Ruziska), entitled "Process For Producing Olefins".

* cited by examiner

*Primary Examiner*—Glenn Caldarola
*Assistant Examiner*—In Suk Bullock

(57) ABSTRACT

A process is described for producing olefins from a vapor product stream from an oxygenate to olefin conversion reaction, the vapor product stream comprising $C_2$ to $C_4$ olefins, $C_5+$ hydrocarbons, at least one oxygenate and water. In the process, the vapor product stream is cooled to remove water therefrom and produce a first vapor effluent stream. The first vapor effluent stream is then cooled and compressed to produce a condensed liquid effluent stream comprising $C_5+$ hydrocarbons and at least one oxygenate, and a residual vapor effluent stream comprising $C_2$ to $C_4$ olefins. At least part of the condensed liquid effluent stream is contacted with a liquid water-containing stream in a liquid-liquid contacting device to at least partly separate said condensed liquid effluent stream, or portion thereof, into an aqueous phase rich in said at least one oxygenate and an organic phase rich in said $C_5+$ hydrocarbons.

101 Claims, 3 Drawing Sheets

PROCESS FOR PRODUCING OLEFINS

FIELD

The present invention relates to a process for producing olefins and, in particular, ethylene and/or propylene.

BACKGROUND

Olefins are traditionally produced from petroleum feedstocks by catalytic or steam cracking processes. These cracking processes, especially steam cracking, produce light olefin(s), such as ethylene and/or propylene, from a variety of hydrocarbon feedstocks. Ethylene and propylene are important commodity petrochemicals useful in a variety of processes for making plastics and other chemical compounds.

The petrochemical industry has known for some time that oxygenates, especially alcohols, are convertible into light olefin(s). There are numerous technologies available for producing oxygenates including fermentation or reaction of synthesis gas derived from natural gas, petroleum liquids or carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Other known syngas production processes include conventional steam reforming, autothermal reforming, or a combination thereof.

The preferred process for converting an oxygenate, such as methanol, into one or more olefin(s), primarily ethylene and/or propylene, involves contacting the feedstock with a catalyst composition, typically containing a molecular sieve catalyst. The product stream from such a process is a complex mixture comprising the desired light olefins, unconverted oxygenates, by-product oxygenates, heavier hydrocarbons and large amounts of water. The separation and purification of this mixture to recover the light olefins and other valuable by-products is critical to the overall efficiency and cost effectiveness of the process. In particular, it is important that the purification scheme produces products that are substantially free of impurities, which could adversely effect downstream processing.

For example, certain oxygenate components present in the product from an oxygenate to olefin conversion (OTO) process, particularly aldehydes and ketones, may cause problems in olefin recovery operations and in derivative manufacturing processes that feed and react $C_4+$ hydrocarbons. Various schemes have therefore been proposed for removing aldehydes and ketones from the olefinic and $C_4+$ hydrocarbon components of oxygenate conversion effluent streams.

U.S. Pat. No. 6,303,841 and U.S. patent application Publication No. 2002/0007101, published Jan. 17, 2002, disclose a process for producing ethylene from oxygenates in which the oxygenate conversion effluent stream is compressed in a multi-stage compressor to a pressure of 1050 to 2860 kPa (150 to 400 psia), preferably 1750 to 2450 kPa (250 to 350 psia), washed with methanol and then water to remove unreacted oxygenates and then contacted with caustic to remove carbon dioxide. The carbon dioxide depleted stream is dried with a solid desiccant and passed to a deethanizer zone to provide a light hydrocarbon feedstream comprising hydrogen, methane, ethylene and ethane, and a deethanized stream comprising propylene, propane, and $C_4+$ olefins. The light hydrocarbon stream is passed to a demethanizer zone operating at a temperature greater than −45° C. to provide a bottom stream comprising ethylene and ethane and an overhead stream comprising hydrogen, methane, and ethylene. The bottom stream is fed to a $C_2$ splitter zone to produce the ethylene product stream and an ethane stream, whereas the overhead stream is fed to a pressure swing adsorption zone to remove hydrogen and methane and produce an ethylene-containing stream which is combined with the oxygenate conversion effluent stream.

U.S. Pat. Nos. 6,403,854 and 6,459,009 to Miller et al. disclose a process for converting oxygenate to light olefins in which the reactor effluent is quenched with an aqueous stream in a two-stage process to facilitate the separation of hydrocarbon gases from any entrained catalyst fines, as well as to remove water and any heavy by-products such as $C_6+$ hydrocarbons. A portion of the waste water stream withdrawn from the bottom of the quench tower is recycled to the quench tower at a point above where the reactor effluent is introduced to the quench tower. The vapor product stream from the quench tower is compressed, passed to an adsorption zone for the selective removal of oxygenates and then passed to a caustic wash zone for removal of carbon dioxide. The resultant carbon dioxide free light olefin stream is passed to a dryer zone for the removal of water and passed to a conventional light olefin recovery zone.

U.S. patent application Publication No. 2003/0130555, published Jul. 10, 2003, discloses a process for separating oxygenated hydrocarbons from the olefin product of an oxygenate to conversion olefins reaction. The product is initially sent to a cooling unit, such as a quench tower, from which cooled olefin product is separated as an olefin vapor stream. The water containing bottoms stream can be recycled through a heat exchanger for cooling and/or removed from the cooling unit to a first separator, such as a distillation column, to provide an oxygenated hydrocarbon product of reduced water content and remaining water as a bottoms product. The olefin vapor stream is compressed to at least 30 psia (207 kPa), preferably 100 to 500 psia (689 to 3447 kPa), and directed to a second separator that provides an olefin vapor product and a liquid oxygenated hydrocarbon-containing stream. The liquid oxygenated hydrocarbon containing stream can then be combined with the water containing bottoms stream or directly added to the first separator to provide an oxygenated hydrocarbon product recovered from the first separator that is reduced in water content and can be used as fuel or co-feed for the oxygenate reaction process. Before or after the compression step, the olefin vapor can be washed with methanol and/or water at a temperature of 40 to 200° F. (4 to 93° C.), preferably 80 to 120° F. (27 to 49° C.).

In addition, U.S. patent application Ser. No. 10/871394, filed Jun. 18, 2004, discloses a process for producing olefins from the vaporous first effluent stream from an oxygenate to olefin conversion reaction, said vaporous first effluent stream comprising $C_2$ and $C_3$ olefins, $C_4$ hydrocarbons, and $C_2$ to $C_6$ carbonyl compounds. In the process, the temperature and pressure of the vaporous first effluent stream are adjusted to produce a second effluent stream having a pressure ranging from about 100 psig to about 350 psig (790 to 2514 kPa) and a temperature ranging from about 70° F. to about 120° F. (21 to 49° C.), wherein the second effluent stream contains about 50 wt. % or more $C_4$ hydrocarbons based upon the total weight of $C_4$ hydrocarbons in the first effluent stream. The second effluent stream is then washed with an alcohol to remove carbonyl compounds and produce a third effluent stream, whereafter the third effluent stream is washed with water to provide a fourth effluent stream comprising the $C_2$ and $C_3$ olefins and about 1.0 wt. % or less of the $C_2$ to $C_6$ carbonyl compounds.

All of the above references are incorporated herein by reference in their entirety.

The unconverted and by-product oxygenates removed from the olefin-containing product streams in the above processes are valuable materials and are generally recycled backed to the OTO reactor for conversion to olefins. However, these oxygenate-containing streams also typically contain heavy ($C_5+$) hydrocarbons, including aromatic compounds, that are considerably less reactive than the other components in the OTO feed and so, if not removed, can build up to unacceptable levels in the the reaction/purification system. Moreover, separation of heavy hydrocarbons from oxygenates, such as methanol, is difficult by conventional fractionation. For example, the normal boiling point of methanol is 140° F. (60° C.), whereas those of hexane and benzene are 156° F. (69° C.) and 176° F. (80° C.) respectively, and conventional fractional distillation would need to employ an expensive column having many trays with high reboiler and condenser duties to make any appreciable separation There is therefore a need for an improved method for separating heavy hydrocarbons from OTO effluent streams.

SUMMARY

In one aspect, the invention relates to a process for producing olefins comprising:

(a) providing a vapor product stream from an oxygenate to olefin conversion reaction comprising $C_2$ to $C_4$ olefins, $C_5+$ hydrocarbons, at least one oxygenate and water;

(b) cooling the vapor product stream to remove water therefrom and produce a first vapor effluent stream;

(c) compressing and cooling the first vapor effluent stream to produce a condensed liquid effluent stream comprising $C_5+$ hydrocarbons and at least one oxygenate and a residual vapor effluent stream comprising $C_2$ to $C_4$ olefins; and (d) contacting at least a portion of the condensed liquid effluent stream with a liquid water-containing stream in a liquid-liquid contacting device to at least partly separate said condensed liquid effluent stream, or portion thereof, into an aqueous phase rich in said at least one oxygenate and an organic phase rich in said $C_5+$ hydrocarbons.

In one embodiment, the vapor product stream in (a) comprises $C_2$ to $C_6$ carbonyls. Conveniently, the first vapor effluent stream comprises from about 0.5 to about 5 wt %, such as from about 1 to about 4 wt %, of said carbonyl compounds. In other alternatives, there is no more than 5 wt. %, such as no more than 2 wt. % water in the first vapor effluent stream, while in others there is at least 0.1 wt. % and no greater than 5 wt/% water.

Conveniently, said at least one oxygenate includes an alcohol, for example methanol, or ethanol, or mixtures thereof. Typically, said vapor product stream in (a) comprises from about 0.1 wt. % to about 20 wt. % methanol, say from about 1 wt. % to about 10 wt. % methanol.

Conveniently, the first vapor effluent stream produced in (b) has a pressure ranging from about 108 kPaa (1 psig) to about 1480 kpaa (200 psig), such as from about 108 kPaa (1 psig) to about 791 kPaa (100 psia), for example from about 136 kPaa (5 psig) to about 377 kPaa (40 psig). Typically, the first vapor effluent stream produced in (b) has a temperature ranging from about 20° C. (68° F.) to about 54° C. (130° F.), such as from about 32° C. (90° F.) to about 43° C. (110° F.).

Conveniently, the residual vapor effluent stream and condensed liquid effluent stream produced in (c) each have a pressure ranging from about 446 kPaa (50 psig) to about 2514 kPaa (350 psig), such as from about 791 kPaa (100 psig) to about 2100 kPaa (290 psig), for example from about 1066 kPaa (140 psig) to about 1342 kPaa (180 psig). Generally, the residual vapor effluent stream and condensed liquid effluent stream produced in (c) are at a temperature ranging from about 20° C. (68° F.) to about 54° C. (130° F.), such as from about 32° C. (90° F.) to about 43° C. (110° F.).

In one embodiment, (c) comprises compressing the first vapor effluent stream, cooling the compressed first vapor effluent stream to form a condensate, and providing the condensate to a vessel to separate the condensed liquid effluent stream and the residual vapor effluent stream. Conveniently, the condensed liquid effluent stream produced in (c) is exposed to one or more reductions in pressure to form a flash liquid effluent stream and a flash vapor effluent stream, and the flash liquid effluent stream is provided as the condensed liquid effluent stream for contacting (d). In a modification, at least a portion of the flash vapor effluent stream is provided along with the first vapor effluent stream for compression and cooling (c). The pressure of the flash liquid effluent stream will be lower than the condensed liquid effluent stream from which it is derived, and conveniently ranges from about 108 kPaa (1 psig) to about 2169 kPaa (300 psig), such as from about 170 kPaa (10 psig) to about 1480 kPaa (200 psig).

In another embodiment, (c) comprises compressing the first vapor effluent stream, cooling the compressed first vapor effluent stream to produce a first condensed liquid effluent stream and a first residual vapor effluent stream, compressing the first residual vapor effluent stream and cooling the compressed first residual vapor effluent stream to produce a second residual vapor effluent stream and a second condensed liquid effluent stream. Thus, the liquid effluent stream produced in (c) and provided for contacting (d) can comprise the first condensed liquid effluent stream, the second condensed liquid effluent stream, portions thereof, or mixtures thereof. Conveniently, the second condensed liquid effluent stream is exposed to one or more reductions in pressure to form a flash liquid effluent stream and a flash vapor effluent stream, and the flash liquid effluent stream is provided as the condensed liquid effluent stream for contacting (d). In a modification at least a portion of the flash vapor effluent stream is provided along with the first residual vapor effluent stream for compression and cooling.

Conveniently, the condensed liquid effluent stream produced in (c) comprises up to about 90 wt. % $C_5+$ hydrocarbon, or up to about 70 wt. % $C_5+$ hydrocarbon, or up to about 50 $C_5+$ hydrocarbon, or up to about 30 wt. % $C_5+$ hydrocarbon. In another aspect, the condensed liquid effluent stream comprises at least about 1 wt. % $C_5+$ hydrocarbon, such as at least about 5 wt. % $C_5+$ hydrocarbon, for example at least about about 10 wt. % $C_5+$ hydrocarbon, more particularly at least about 20 wt. % $C_5+$ hydrocarbon. Advantageously, the condensed liquid effluent stream comprises no more than about 40 wt. % aromatics, such as no more than about 30 wt. % aromatics, more specifically no more than about 20 wt. % aromatics, for example no more than about 10 wt. % aromatics, including no more than about 5 wt. % aromatics, and generally at least about 0.1 wt. % aromatics, for example at least about 1 wt. % aromatics, such as a least about 2 wt. % aromatics, more particularly at least about 4 wt. % aromatics.

In another embodiment, the condensed liquid effluent stream produced in (c) comprises no more than about 10 wt.

% benzene, such as no more than about 5 wt. % benzene, for example no more than about 1 wt. % benzene, including no more than about 0.5 wt. % benzene, more specifically no more than about 0.1 wt. % benzene. Conveniently, the condensed liquid effluent stream comprises no more than about 50 wt. % $C_5+$ saturates, such as no more than about 30 wt. % $C_5+$ saturates, including no more than about 10 wt. % $C_5+$ saturates, for example no more than about 5 wt. % $C_5+$ saturates, and typically at least about 0.1 wt. % $C_5+$ saturates, for example at least about 1 wt. % $C_5+$ saturates, such as a least about 2 wt. % $C_5+$ saturates, more particularly at least about 4 wt. % $C_5+$ saturates. Conveniently, the condensed liquid effluent stream comprises at least about 1 wt. % oxygenate, such as at least about 5 wt. % oxygenate, for example at least about 10 wt. % oxygenate, more specifically at least about 20 wt. % oxygenate, including at least about 30 wt. % oxygenate.

In another embodiment, the at least one oxygenate in the vapor product stream is one or more $C_2$ to $C_6$ carbonyl species, for example, ethanal, or acetone, or mixtures thereof. Conveniently, the condensed liquid effluent stream produced in (c) comprises at least about 0.1 wt. % $C_2$ to $C_6$ carbonyls, or at least about 1 wt. % $C_2$ to $C_6$ carbonyls, or at least about 2 wt. % $C_2$ to $C_6$ carbonyls, or at least about 5 wt. % $C_2$ to $C_6$ carbonyls, or at least about 10 wt. % $C_2$ to $C_6$ carbonyls.

Conveniently, the contacting (d) comprises feeding the water-containing wash liquid to the liquid-liquid contacting device at a first rate and feeding the condensed stream to the liquid-liquid contacting device at a second rate. The weight ratio of the second rate to the first rate ranges from about 0.1 to about 10, such as from about 0.2 to about 2, for example about 0.3 to about 1.4, such as about 0.6 to about 1.2. Where, said at least one oxygenated hydrocarbon includes methanol, the weight ratio of methanol in the second rate to the first rate ranges from about 0.1 to about 1, such as from about 0.2 to about 0.7, for example from about 0.3 to about 0.6.

Conveniently, the liquid water-containing stream comprises at least about 80 wt. % water, more particularly at least about 90 wt. % water, such as at least about 95 wt. % water, for example at least about 99 wt. % water.

Conveniently, the organic phase produced in (d) comprises up to about 95 wt. % $C_5+$ hydrocarbons, or up to about 75 wt. % $C_5+$ hydrocarbons, or up to about 60 wt. % $C_5+$ hydrocarbons, or up to about 50 wt. % $C_5+$ hydrocarbons. Typically, the organic phase comprises at least about 1 wt. % $C_5+$ saturates, such as at least about 5 wt. % $C_5+$ saturates, for example at least about 10 wt. % $C_5+$ saturates, and generally no greater than about 60 wt. % $C_5+$ saturates, more specifically no greater than about 40 wt. % $C_5+$ saturates, such as no greater than about 30 wt. % $C_5+$ saturates. Generally, the organic phase comprises at least about 0.1 wt. % aromatics, such as at least about 0.5 wt. % aromatics, including at least about 1 wt. % aromatics, more particularly at least about at least about 2 wt. % aromatics, and typically no greater than about 30 wt. % aromatics, for example no greater than about 20 wt. % aromatics, including no greater than about 10 wt. % aromatics, such as no greater than about 5 wt. % aromatics. Conveniently, the organic phase comprises at least about 0.01 wt. % benzene, such as at least about 0.05 wt. % benzene, including at least about 0.1 wt. % benzene, and typically no greater than about 3 wt. % benzene, for example no greater than about 2 wt. % benzene, including no greater than about 1 wt. % benzene.

Conveniently, the aqueous phase comprises at least about 25 wt. % water, for example at least about 40 wt. % water, such as at least about 50 wt. % water, more particularly at least about 60 wt. % water.

Conveniently, the aqueous phase comprises at least about 1 wt. % of the at least one oxygenate, for example at least about 10 wt. % of the at least one oxygenate, such as at least about 20 wt. % of the at least one oxygenate, and generally no greater than about 60 wt. % of the at least one oxygenate, such as no greater than about 50 wt. % of the at least one oxygenate, including no greater than about 35 wt. % of the at least one oxygenate.

Conveniently, the aqueous phase comprises at least about 1 wt. % of $C_2$ to $C_6$ carbonyls, for example at least about 10 wt. % of $C_2$ to $C_6$ carbonyls, such as at least about 20 wt. % of $C_2$ to $C_6$ carbonyls, and generally no greater than about 60 wt. % of $C_2$ to $C_6$ carbonyls, such as no greater than about 50 wt. % of $C_2$ to $C_6$ carbonyls, including no greater than about 35 wt. % of $C_2$ to $C_6$ carbonyls.

Conveniently, said contacting (d) is conducted within said liquid-liquid contacting device at a pressure of from about 170 kPaa (10 psig) to about 2514 kpaa (350 psig), such as from about 446 kPaa (50 psig) to about 1480 kpaa (200 psig). Conveniently, said contacting (d) is conducted within said liquid-liquid contacting device at a temperature of from about 1° C. (34° F.) to about 54° C. (130° F.), for example from about 21° C. (70° F.) to about 43° C. (110° F.).

In one embodiment, the process further comprises fractionating the aqueous phase produced in (d) into a water-rich fraction and a fraction rich in said at least one oxygenated hydrocarbon. If desired, at least part of said fraction rich in said at least one oxygenated hydrocarbon is recycled to said oxygenate to olefin conversion reaction. Further, if desired, at least a part of the water-rich fraction can be used as at least a portion of the liquid water-containing stream for liquid-liquid contacting.

In a further aspect, the invention resides in a process for producing olefins comprising:
  (a) providing a vapor product stream from an oxygenate to olefin reaction comprising $C_2$ to $C_4$ olefins, $C_5+$ hydrocarbons, at least one oxygenate and water;
  (b) cooling the vapor product stream to remove water therefrom and produce a first vapor effluent stream;
  (c) compressing and cooling the first vapor effluent stream to produce a second effluent stream that is at least partially in the vapor state;
  (d) washing at least part of the second effluent stream with a liquid alcohol-containing stream to remove at least a portion of at least one oxygenate from the second effluent stream in a wash liquid effluent stream, and produce a wash vapor effluent stream comprising $C_2$ to $C_4$ olefins, the wash liquid effluent stream further comprising $C_5+$ hydrocarbons and alcohol from the liquid alcohol-containing stream; and
  (e) contacting at least a portion of the wash liquid effluent stream with a liquid water-containing stream in a liquid-liquid contacting device to at least partially separate said wash liquid effluent stream, or portion thereof, into an aqueous phase rich in said at least one oxygenate and said alcohol from the liquid alcohol-containing stream, and an organic phase rich in said $C_5+$ hydrocarbons.

Conveniently, the liquid alcohol-containing stream comprises methanol and/or ethanol, and preferably methanol.

Conveniently, the second effluent stream produced in (c) has a pressure ranging from about 446 kPaa (50 psig) to about 2514 kPaa (350 psig), such as from about 791 kPaa (100 psig) to about 2100 kPaa (290 psig), for example from about 1066 kPaa (140 psig) to about 1342 kPaa (180 psig). Generally, the second effluent stream produced in (c) has a temperature ranging from about 20° C. (68° F.) to about 54° C. (130° F.), such as from about 32° C. (90° F.) to about 43° C. (110° F.).

Conveniently, the wash liquid effluent stream produced in (d) has a pressure ranging from about 446 kPaa (50 psig) to about 2514 kPaa (350 psig), such as from about 791 kPaa (100 psig) to about 2100 kPaa (290 psig), for example from about 1066 kPaa (140 psig) to about 1342 kPaa (180 psig). Generally, the wash liquid effluent stream produced in (d) has a temperature ranging from about 20° C. (68° F.) to about 54° C. (130° F.), such as from about 32° C. (90° F.) to about 43° C. (110° F.).

Conveniently, the wash liquid effluent stream produced in (d) comprises up to about 90 wt. % $C_5+$ hydrocarbon, or up to about 70 wt. % $C_5+$ hydrocarbon, or up to about 50 $C_5+$ hydrocarbon, or up to about 30 wt. % $C_5+$ hydrocarbon. Typically, the wash liquid effluent stream comprises at least about 1 wt. % $C_5+$ hydrocarbon, such as at least about 5 wt. % $C_5+$ hydrocarbon, for example at least about about 10 wt. % $C_5+$ hydrocarbon, more particularly at least about 20 wt. % $C_5+$ hydrocarbon. Conveniently, the wash liquid effluent stream comprises no more than about 40 wt. % aromatics, such as no more than about 30 wt. % aromatics, more specifically no more than about 20 wt. % aromatics, for example no more than about 10 wt. % aromatics, including no more than about 5 wt. % aromatics, and generally at least about 0.1 wt. % aromatics, for example at least about 1 wt. % aromatics, such as a least about 2 wt. % aromatics, more particularly at least about 4 wt. % aromatics.

Conveniently, the wash liquid effluent stream produced in (d) comprises no more than about 10 wt. % benzene, such as no more than about 5 wt. % benzene, for example no more than about 1 wt. % benzene, including no more than about 0.5 wt. % benzene, more specifically no more than about 0.1 wt. % benzene. Generally, the wash liquid effluent stream comprises no more than about 50 wt. % $C_5+$ saturates, such as no more than about 30 wt. % $C_5+$ saturates, including no more than about 10 wt. % $C_5+$ saturates, for example no more than about 5 wt. % $C_5+$ saturates, and typically at least about 0.1 wt. % $C_5+$ saturates, for example at least about 1 wt. % $C_5+$ saturates, such as a least about 2 wt. % $C_5+$ saturates, more particularly at least about 4 wt. % $C_5+$ saturates.

In one embodiment, the wash liquid effluent stream produced in (d) comprises at least about 1 wt. % oxygenate, such as at least about 5 wt. % oxygenate, for example at least about 10 wt. % oxygenate, more specifically at least about 20 wt. % oxygenate, including at least about 30 wt. % oxygenate.

Conveniently, the wash liquid effluent stream produced in (d) comprises at least about 5 wt. %, such as at least about 10 wt. %, for example at least about 20 wt. %, more particularly at least about 30 wt. %, alcohol from the liquid alcohol-containing stream. Suitably, the wash liquid effluent stream comprises no greater than about 90 wt. %, for example no greater than about 75 wt. %, such as no greater than about 60 wt. % alcohol from the liquid alcohol-containing stream.

Conveniently, the wash liquid effluent stream produced in (d) comprises at least about 0.1 wt. % $C_2$ to $C_6$ carbonyls, or at least about 1 wt. % $C_2$ to $C_6$ carbonyls, or at least about 2 wt. % $C_2$ to $C_6$ carbonyls, or at least about 5 wt. % $C_2$ to $C_6$ carbonyls, or at least about 10 wt. % $C_2$ to $C_6$ carbonyls.

In one embodiment the compression and cooling (c) comprises compressing the first vapor effluent stream and cooling the compressed first vapor effluent stream to produce a first condensed liquid effluent stream and a first residual vapor effluent stream. The first residual vapor effluent stream is compressed and cooled to produce a second effluent stream that is at least partially in the vapor state, and the second effluent stream is provided for the washing (d). Optionally, the second effluent stream is segregated into a second condensed liquid effluent stream and a second residual vapor effluent stream, with the second residual vapor effluent stream being provided for the washing (d).

In an embodiment, the wash liquid effluent stream produced in (d) is exposed to one or more reductions in pressure to form a wash flash liquid effluent stream and a wash flash vapor effluent stream, and the wash flash liquid effluent stream is provided as the wash liquid effluent stream for contacting (e). In a modification, at least a portion of the wash flash vapor effluent stream is provided along with the first vapor effluent stream for compression and cooling (c). Optionally, at least a portion of the wash flash vapor effluent is provided for compression and cooling along with the first residual vapor effluent. The pressure of the wash flash liquid effluent stream will be lower than that of the wash liquid effluent stream from which it is derived, and conveniently ranges from about 108 kPaa (1 psig) to about 2169 kPaa (300 psig), such as from about 170 kPaa (10 psig) to about 1480 kPaa (200 psig).

In yet another aspect, the invention resides in a process for producing olefins comprising:

(a) providing a vapor product stream from an oxygenate to olefin reaction comprising $C_2$ to $C_4$ olefins, $C_5+$ hydrocarbons, at least one oxygenate and water;

(b) cooling the vapor product stream to remove water therefrom and produce a first vapor effluent stream;

(c) compressing and cooling the first vapor effluent stream to produce a condensed liquid effluent stream comprising C5+ hydrocarbons and at least one oxygenate and a residual vapor effluent stream comprising $C_2$ to $C_4$ olefins;

(d) washing at least part of the residual vapor effluent stream with a liquid alcohol-containing stream to produce a wash vapor effluent stream comprising $C_2$ to $C_4$ olefins, and a wash liquid effluent stream comprising said at least one oxygenate and said $C_5+$ hydrocarbons; and (e) contacting at least a portion of the condensed liquid effluent stream produced in (c) and at least a portion of the wash liquid effluent stream produced in (d) with a liquid water-containing stream in a liquid-liquid contacting device to at least partially separate said condensed liquid effluent stream produced in (c) and saud wash liquid effluent stream produced in (d), or portions thereof, into an aqueous phase rich in said at least one oxygenate and alcohol contained in the liquid alcohol containing stream, and an organic phase rich in said $C_5+$ hydrocarbons.

In one embodiment, said condensed liquid effluent stream in (c) and said wash liquid effluent stream in (d), or portions thereof, are combined, and said combined stream, or a portion thereof, is provided for contacting (e).

Alternatively, the condensed liquid effluent stream in (c) and the wash liquid effluent stream in (d), or portions thereof, are combined, and the combined stream, or a portion thereof, is exposed to one or more reductions in pressure to form a flash liquid effluent stream. The flash liquid effluent stream is provided as the portion of the wash liquid effluent stream for contacting (e).

Conveniently, the compression and cooling (c) comprises compressing the first vapor effluent stream, and cooling the compressed first vapor effluent stream to produce a first condensed liquid effluent stream and a first remaining vapor effluent stream. The first remaining vapor effluent stream is compressed and cooled to produce a second effluent stream that is at least partially in the vapor state, said second effluent stream being provided for said washing (d). Optionally, the second effluent stream is segregated into a second condensed liquid effluent stream and a second residual vapor effluent stream, with the second residual vapor effluent stream is provided for washing (d).

In a modification, the first condensed liquid effluent stream, second condensed liquid effluent stream or wash liquid effluent stream, or portions thereof, is exposed to one or more reductions in pressure to form a flash liquid effluent stream, wherein said flash liquid effluent stream is provided as at least a portion of the condensed liquid effluent stream and wash liquid effluent stream for contacting (e).

Optionally, one or more of the liquid effluent streams, or portions thereof are mixed prior to the reduction in pressure. In a more specific embodiment of this type, the second condensed liquid effluent stream and the wash liquid effluent stream, or portions thereof, are exposed to a reduction in pressure along with the compressed first vapor effluent stream to produce a first residual vapor effluent stream and a common first condensed liquid effluent stream and first flash liquid effluent stream. This common first condensed liquid effluent stream and first flash liquid effluent stream is exposed to a further reduction in pressure to produce a second flash liquid effluent stream that provided as at least a portion of the condensed liquid effluent stream and wash liquid effluent stream for contacting (e).

As used herein, the term "$C_x$ hydrocarbon" indicates aliphatic, olefin, diolefin, acetylene, or cyclic variations thereof, or aromatic hydrocarbon molecules having the number of carbon atoms represented by the subscript "x" Similarly, the term "$C_x$-containing stream" means the stream contains $C_x$ hydrocarbon. The more specific molecule is represented by a more explicit term in place of "hydrocarbon", so that, for example, "$C_4$ olefin" indicates butene-1, or butene-2, or isobutene, or combinations thereof. The term "$C_x$+hydrocarbons" indicates those molecules noted above having the number of carbon atoms represented by the subscript "x" or greater. For example, "$C_4$+hydrocarbons" would include $C_4$, $C_5$ and higher carbon number hydrocarbons. Similarly "$C_x$-hydrocarbons" indicates those molecules noted above having the number of carbon atoms represented by the subscript "x" or fewer. As used herein, hydrocarbons do not contain an oxygen molecule and thus are not to be confused with the term oxygenate or its various more specific forms, such as alcohol, ether, aldehyde, ketone or carbonyl.

As used herein, the term "aromatic" has the classical chemistry meaning of a hydrocarbon molecule containing the six-carbon ring characteristic of the benzene series and related organic groups. Examples of aromatics include, but are not limited to single ring compounds such as benzene, and their alkyl substituted forms such as toluene, xylenes such as ortho-xylene and para-xylene, cumene and durene. Aromatics also includes condensed aromatic ring molecules such as naphthalene and alkyl substituted forms thereof. An oxygen atom may be present in an aromatic molecule, such as phenol, but such an aromatic specie is not to be confused with the term oxygenate as used herein. Further, an aromatic molecule is considered to be within the potential scope of the more general term $C_5$+ hydrocarbons.

As used herein, the term "$C_2$ to $C_6$ carbonyl compounds" is defined as meaning one or more molecules containing from 2 to 6 carbon atoms that further comprise at least one oxygen atom in an aldehyde (oxygen that has a double bond to a carbon atom that in turn has a single bond to one other carbon atom and one hydrogen atom) or ketone (oxygen that has double bond to a carbon atom that in turn has a single bond to each of two other carbon atoms) moiety.

DETAILED DESCRIPTION OF THE EMBODIMENTS

Figure 1:
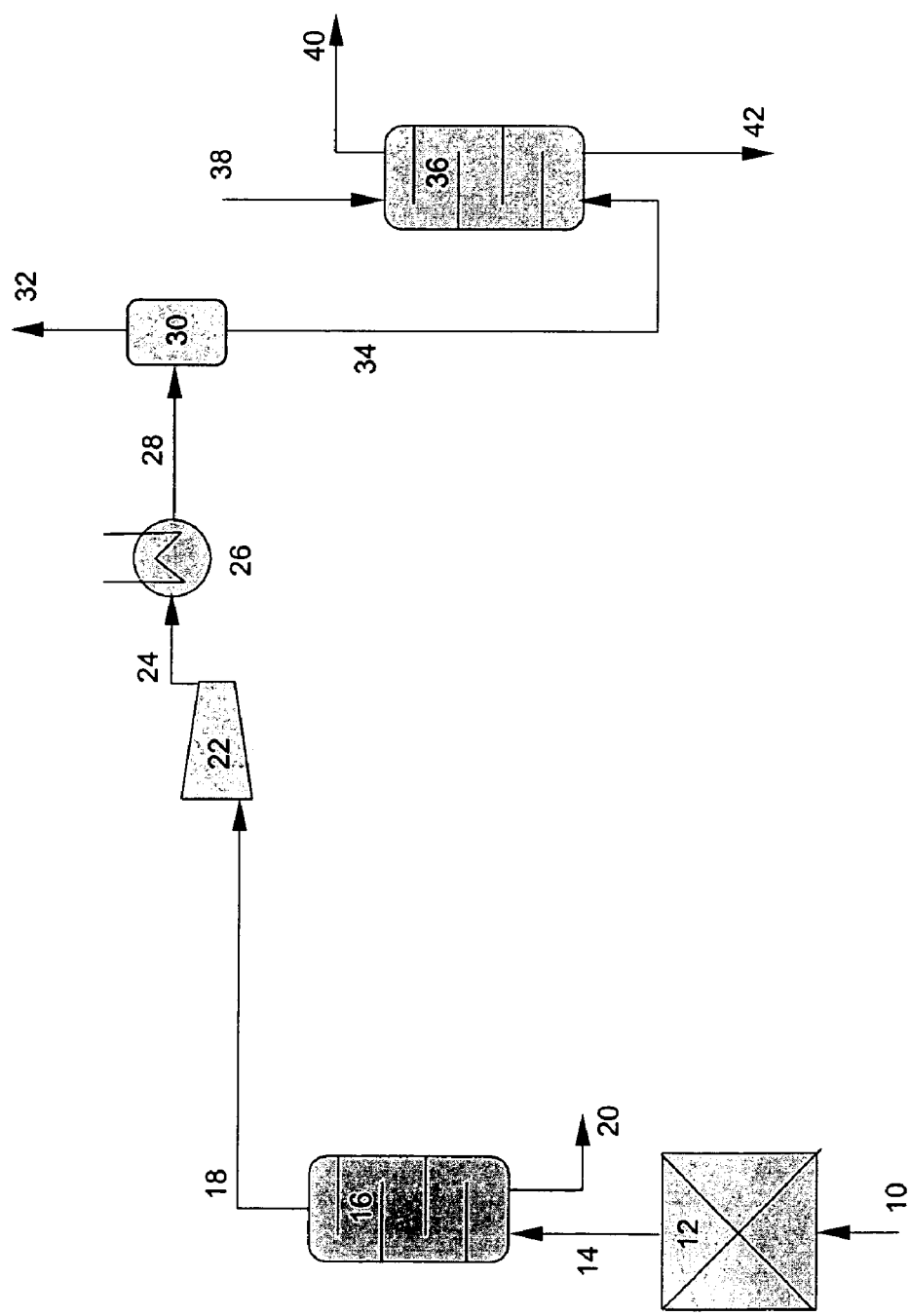
FIG. 1 is a schematic flow diagram illustrating a process according to a first example of the invention.

Molecular Sieves and Catalysts Thereof for Use in OTO Conversion

Molecular sieves suited to use for converting oxygenates to olefins (OTO) have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the *Atlas of Zeolite Framework Types*, 5th edition, Elsevier, London, England (2001), which is herein fully incorporated by reference.

Non-limiting examples of these molecular sieves are the small pore molecular sieves of a framework-type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof, the medium pore molecular sieves of a framework-type selected from the group consisting of AFO, AEL, EUO, HEU, FER, MEL, MFI, MTW, MTT, TON, and substituted forms thereof; and the large pore molecular sieves of a framework-type selected from the group consisting of EMT, FAU, and substituted forms thereof. Other molecular sieves have a framework-type selected from the group consisting of ANA, BEA, CFI, CLO, DON, GIS, LTL, MER, MOR, MWW and SOD. Non-limiting examples of the preferred molecular sieves, particularly for converting an oxygenate containing feedstock into olefin(s), include those having a framework-type selected from the group consisting of AEL, AFY, BEA, CHA, EDI, FAU, FER, GIS, LTA, LTL, MER, MFI, MOR, MTT, MWW, TAM and TON. In one embodiment, the molecular sieve used in the process of the invention has an AEI topology or a CHA topology, or a combination thereof, preferably a CHA topology.

Molecular sieve materials all have 3-dimensional, four-connected framework structure of corner-sharing $TO_4$ tetrahedra, where T is any tetrahedrally coordinated cation.

These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1-67, Elsevier Science, B.V., Amsterdam, Netherlands (2001).

The small, medium and large pore molecular sieves have from a 4-ring to a 12-ring or greater framework-type. In one embodiment, the molecular sieves used herein have 8-, 10- or 12-ring structures or larger and an average pore size in the range of from about 3 Å to 15 Å. More typically, the molecular sieves utilized in the invention, such as silicoaluminophosphate molecular sieves, have 8-rings and an average pore size less than about 5 Å, such as in the range of from 3 Å to about 5 Å, for example from 3 Å to about 4.5 Å, particularly from 3.5 Å to about 4.2 Å.

Molecular sieves used herein typically have two or more [SiO$_4$], [AlO$_4$] and/or [PO$_4$] tetrahedral units. These silicon, aluminum and/or phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO), EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. No. 4,824,554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, SAPO$_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), International Patent Publication No. WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

The more preferred silicon, aluminum and/or phosphorous containing molecular sieves include aluminophosphate (ALPO) molecular sieves, silicoaluminophosphate (SAPO) molecular sieves and substituted, preferably metal substituted, forms thereof. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(MAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanides of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Publication No. 2002/0165089 published Nov. 7, 2002 and International Patent Publication No. WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

The molecular sieves useful for oxygenates to olefins conversion processes are synthesized and then made or formulated into catalysts by combining the synthesized molecular sieves with a binder and/or a matrix material to form a molecular sieve catalyst composition. This molecular sieve catalyst composition is formed into useful shaped and sized particles by well-known techniques such as spray drying, pelletizing, extrusion, and the like.

Oxygenate to Olefins (OTO) Process

The feedstock to an oxygenate to olefins process comprises one or more oxygenates, more specifically, one or more organic compound(s) containing at least one oxygen atom. Typically, the oxygenate in the feedstock comprises one or more alcohol(s), generally aliphatic alcohol(s) where the aliphatic moiety of the alcohol(s) has from 1 to 20 carbon atoms, such as from 1 to 10 carbon atoms, and conveniently from 1 to 4 carbon atoms. The alcohols useful as feedstock in an oxygenate to olefins process include lower straight and branched chain aliphatic alcohols and their unsaturated counterparts.

Non-limiting examples of suitable oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. Typically, the feedstock is selected from one or more of methanol, ethanol, dimethyl ether and diethyl ether, especially methanol and dimethyl ether, and preferably methanol.

In addition to the oxygenate component, such as methanol, the feedstock may contains one or more diluent(s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve catalyst composition. Diluent(s) may comprise from about 1 mole % to about 99 mole % of the total feedstock.

In the OTO process, the various feedstocks discussed above, particularly a feedstock containing an alcohol, are converted over a molecular sieve catalyst, primarily into one or more olefin(s). The olefin(s) or olefin monomer(s) produced from the feedstock typically have from 2 to 30 carbon atoms, such as 2 to 8 carbon atoms, for example 2 to 6 carbon atoms, especially 2 to 4 carbons atoms, and preferably are ethylene and/or propylene.

The present process can be conducted over a wide range of temperatures, such as in the range of from about 200° C. to about 1000° C., for example from about 250° C. to about 800° C., including from about 250° C. to about 750° C., conveniently from about 300° C. to about 650° C., typically from about 350° C. to about 600° C. and particularly from about 350° C. to about 550° C.

Similarly, the present process can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

The weight hourly space velocity (WHSV), defined as the total weight of feedstock excluding any diluents per hour per weight of molecular sieve in the catalyst composition, typically ranges from about 1 $hr^{-1}$ to about 5000 $hr^{-1}$, such as from about 2 $hr^{-1}$ to about 3000 $hr^{-1}$, for example from about 5 $hr^{-1}$ to about 1500 $hr^{-1}$, and conveniently from about 10 $hr^{-1}$ to about 1000 $hr^{-1}$. In one embodiment, the WHSV is greater than 20 $hr^{-1}$ and, where feedstock contains methanol and/or dimethyl ether, is in the range of from about 20 $hr^{-1}$ to about 300 $hr^{-1}$.

Where the process is conducted in a fluidized bed, the superficial gas velocity (SGV) of the feedstock including diluent and reaction products within the reactor system, and particularly within a riser reactor(s), is at least 0.1 meter per second (m/sec), such as greater than 0.5 m/sec, such as greater than 1 m/sec, for example greater than 2 m/sec, conveniently greater than 3 m/sec, and typically greater than 4 m/sec.

The process of the invention is conveniently conducted as a fixed bed process, or more typically as a fluidized bed process (including a turbulent bed process), such as a continuous fluidized bed process, and particularly a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor types are riser reactors generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one practical embodiment, the process is conducted as a fluidized bed process or high velocity fluidized bed process utilizing a reactor system, a regeneration system and a recovery system.

In such a process the reactor system would conveniently include a fluid bed reactor system having a first reaction zone within one or more riser reactor(s) and a second reaction zone within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent(s), is fed to the one or more riser reactor(s) into which a molecular sieve catalyst composition or coked version thereof is introduced. In one embodiment, prior to being introduced to the riser reactor(s), the molecular sieve catalyst composition or coked version thereof is contacted with a liquid, preferably water or methanol, and/or a gas, for example, an inert gas such as nitrogen.

In an embodiment, the amount of liquid feedstock fed separately or jointly with a vapor feedstock, to the reactor system is in the range of from 0.1 weight percent to about 85 weight percent, such as from about 1 weight percent to about 75 weight percent, for example from about 5 weight percent to about 65 weight percent based on the total weight of the feedstock including any diluent contained therein. The liquid and vapor feedstocks are preferably of similar or the same composition, or contain varying proportions of the same or different feedstock with the same or different diluent.

The feedstock entering the reactor system is preferably converted, partially or fully, in the first reactor zone into a gaseous product stream that enters the disengaging vessel along with the coked catalyst composition. In the preferred embodiment, cyclone(s) are provided within the disengaging vessel to separate the coked catalyst composition from the gaseous product stream containing one or more olefin(s) within the disengaging vessel. Although cyclones are preferred, gravity effects within the disengaging vessel can also be used to separate the catalyst composition from the gaseous product stream. Other methods for separating the catalyst composition from the gaseous product stream include the use of plates, caps, elbows, and the like.

In one embodiment, the disengaging vessel includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to the regeneration system.

The coked catalyst composition is withdrawn from the disengaging vessel and introduced to the regeneration system. The regeneration system comprises a regenerator where the coked catalyst composition is contacted with a regeneration medium, preferably a gas containing oxygen, under conventional regeneration conditions of temperature, pressure and residence time.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide arid/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450° C. to about 750° C., and conveniently from about 550° C. to 700° C. The regeneration pressure may be in the range of from about 15 psia (103 kPaa) to about 500 psia (3448 kPaa), such as from about 20 psia (138 kPaa) to about 250 psia (1724 kPaa), including from about 25 psia (172 kPaa) to about 150 psia (1034 kPaa), and conveniently from about 30 psia (207 kPaa) to about 60 psia (414 kPaa).

The residence time of the catalyst composition in the regenerator may be in the range of from about one minute to several hours, such as from about one minute to 100 minutes, and the volume of oxygen in the regeneration gas may be in the range of from about 0.01 mole percent to about 5 mole percent based on the total volume of the gas.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system. Other methods for operating a regeneration system are disclosed in U.S. Pat. No. 6,290,916 (controlling moisture), which is herein fully incorporated by reference.

The regenerated catalyst composition withdrawn from the regeneration system, preferably from a catalyst cooler, is combined with a fresh molecular sieve catalyst composition and/or re-circulated molecular sieve catalyst composition and/or feedstock and/or fresh gas or liquids, and returned to the riser reactor(s). In one embodiment, the regenerated catalyst composition withdrawn from the regeneration system is returned to the riser reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more riser reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, *Experimental Techniques, Circulating Fluidized Beds*, Grace, Avidan and Knowlton, eds., Blackie, 1997 (336-337), which is herein incorporated by reference.

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example from about 0.2 weight percent to about 5 weight percent, and conveniently from about 0.3 weight percent to about 2 weight percent based on the weight of the molecular sieve.

The gaseous product stream is withdrawn from the disengaging system and passed to a recovery system for separating and purifying the olefins and other useful components in the product stream.

OTO Product Recovery Process

The vapor product stream from the oxygenate to olefin conversion process described above is a complex mixture comprising $C_2$ to $C_4$ olefins, $C_5$+ hydrocarbons, unconverted oxygenates, by-product oxygenates (including $C_2$ to $C_6$ aldehydes and ketones), heavier hydrocarbons (including aromatics, such as benzene) and large amounts of water.

On leaving the OTO reactor system, the vapor product stream is at reaction temperature and pressure and hence is initially cooled in a quench device. The quench device removes heat from the vapor product stream, and may comprise a traditional indirect heat exchanger, for example using cooling water or air on the shell or open side with the vapor product stream within tubes, or a direct contact device such as a traditional quench tower employing water as the quench medium. As a result of this cooling, water from the vapor product stream will condense to the liquid phase while the bulk of the hydrocarbons remain in the vapor phase. The liquid water phase is then separated from the vapor phase by conventional means. In an indirect heat exchanger, for example, the water may be collected and removed from a boot provided at the bottom of the exchanger shell, or the entire condensed vapor product stream may be passed to a vessel, such as a drum, to provide such liquid-vapor separation. In the quench tower, the water may be collected in and exit from the bottom of the tower shell. In any case, most of the water (generally at least 90 wt %) in the vapor product stream is condensed and is removed from the bottom of the quench device as a liquid water-rich bottoms stream. The light hydrocarbons and light oxygenates in the product stream are removed from the top of the heat exchanger or quench tower as a first vapor effluent stream at a first pressure.

The liquid water-rich bottoms stream from the quench device will contain various other materials in addition to water, such as unreacted oxygenate feedstock, e.g., methanol, and other oxygenates created as byproducts of the oxygenate to olefins reaction, for example, but not limited to, ethanol, ethanal, propanal, acetone, butanone, dimethyl ether, methyl ethyl ether, acetic acid and propionic acid. The proportions of these oxygenates in the water-rich bottoms stream may vary widely dependent upon the nature of the oxygenate to olefin reactor, including feedstock, catalyst, WHSV, temperature and pressure. Further, the proportions of these oxygenates in the water-rich bottoms stream may vary widely dependent upon the specifics of the quench tower, such as the pressure, temperature and height of the tower and nature of the exchanger or tower internals.

Regardless of the exact composition, the liquid water-rich bottoms stream will need to undergo further processing to provide components in an appropriate state for use or further treatment, e.g., provide a water stream low enough in organic content for typical water waste treatment, or provide an oxygenate stream low enough in water content for use as fuel or for addition to some point in the oxygenate to olefins process or apparatus. Examples of such treatment can be found in U.S. Pat. Nos. 6,121,504, 6,403,854 and 6,459,009 and U.S. patent application Ser. No. 10/720,505 filed Nov. 24, 2003.

In one embodiment, the liquid water-rich bottoms stream is directed to a water-oxygenate fractionation tower, e.g., a water-methanol fractionation tower, which is operated to separate methanol and other oxygenates as an overhead, e.g., greater than about 20 wt % oxygenates (with the balance being largely water), and substantially pure water as a bottoms stream, typically, greater than about 90 wt % water, say, greater than about 95 wt % water, e.g., greater than about 99 wt % water. The overhead product of the fractionation tower, being a fraction rich in at least one oxygenate, can be used for various purposes, including as a feedstock to the OTO reactor along with the primary oxygenate feedstock. If the fraction rich in at least one oxygenate is taken as a vapor, this provides vaporized methanol/oxygenate feed to the reactor with virtually no incremental heat input beyond that already required in the reboiler of the methanol-water fractionation tower, with no incremental heat load in the primary feed vaporization section of the OTO reactor.

The first vapor effluent stream exiting as overhead from the quench tower is typically at an initial pressure of from about 1 psig to about 200 psig (108 to 1480 kPaa), more specifically from about 1 psig to about 100 psig (108 to 791 kPaa), such as from about 5 psig to about 80 psig (136 to 653 kPa), for example from about 5 psig to about 40 psig (136 to 377 kPa). Conveniently, the temperature of the first vapor effluent stream is at least 80° F. (27° C.), such as at least about 90° F. (32° C.), and generally no more than 130° F. (54° C.), such as no more than 110° F. (43° C.), for example no more than 100° F. (38° C.). The first vapor effluent stream normally comprises from about 0.5 to about 5 wt %, such as from about 1 to about 4 wt %, of $C_2$ to $C_6$ carbonyl compounds and no more than 10 wt %, for example no more than 5 wt %, such as no more than 2 wt %, water.

After exiting the quench device, the first vapor effluent stream is in communication with a vapor compression device, conveniently a traditional mechanical reciprocating, centrifugal or axial compressor. Even non-mechanical devices like an ejector, such as a steam ejector, may be used, but are not preferred. The communication typically includes passage through a pipe, potentially further comprising other process elements such as vessels, instrumentation (e.g. a flow metering orifice plate) or valves, such as control valves. Such communication will cause a reduction in the pressure of the first vapor effluent prior to reaching the suction of the compression device at a first suction pressure. Generally the communication path is designed to preserve as much pressure of the first vapor effluent stream as practical, thus saving compression costs. The first vapor effluent stream is then compressed, typically to a pressure that is greater than that of the first vapor effluent stream, and cooled, for example in an indirect heat exchanger. Optionally, multiple stages of compression and cooling may be used.

The compression and cooling of the first vapor effluent stream causes partial condensation thereof so as to produce a second effluent stream that is partially in the vapor state. This second effluent stream comprises the condensed liquid effluent stream and the residual vapor effluent stream. The second effluent liquid stream can be separated, for example in a knock-out drum (into which a heat exchanger for cooling may be integrated), to provide an individual condensed liquid effluent stream discrete from the residual vapor effluent stream. The residual vapor stream contains the lighter components, including desired $C_2$ to $C_4$ olefins and some of the lower molecular weight oxygenates, $C_2$ to $C_6$ carbonyl compounds and $C_5$+ hydrocarbons, from the first vapor effluent stream. The condensed liquid effluent stream contains heavier components, including a significant proportion of oxygenates, including unreacted feed, and $C_2$ to $C_6$ carbonyl compounds, and $C_5$+ hydrocarbons.

Where the compression and cooling of the first vapor effluent stream occurs in a plurality of stages, partial condensation and separation of condensed liquid effluent streams and residual vapor effluent streams from the first effluent stream conveniently occurs at each compression stage, conveniently in a knock-out drum provided after each compression/cooling stage. Thus, for example, a first compression and cooling action will provide a first condensed liquid effluent stream and a first residual vapor stream; the first remaining vapor stream is then subjected to another compression and cooling stage to create a second liquid effluent stream that is at least partially in the vapor state, that may then be segregated to provide a second liquid effluent stream and a second residual vapor stream. The residual vapor effluent stream and condensed liquid effluent stream exiting the or each compression/cooling stage are generally at a pressure greater than that of the first effluent stream, with a temperature that promotes the desired extent of partial condensation to generate the desired rates and compositions of the residual vapor effluent stream and condensed liquid effluent stream.

In one embodiment, the second effluent stream or residual vapor effluent stream (or streams) is subjected to a washing step in which the given stream is washed with a liquid alcohol-containing stream in a vapor-liquid contacting device. This washing step is effective to remove $C_2$ to $C_6$ carbonyl compounds from the second effluent stream and residual vapor stream, and produces a wash vapor effluent stream containing the desired $C_2$ to $C_4$ olefins. It also produces a wash liquid effluent stream comprising the $C_2$ to $C_6$ carbonyl compounds and substantial quantities of $C_5+$ hydrocarbons and the alcohol from the liquid alcohol containing stream.

Conveniently, said liquid alcohol-containing stream used in the washing step comprises methanol and/or ethanol, and preferably methanol. Although the methanol employed can contain water and traces (such as less than 2 wt %, or less than 1 wt %, or less than 0.5 wt % or less than 0.1 wt %), of other alcohols and hydrocarbons, methanol is more effective than water and other alcohols in removing such carbonyl species from hydrocarbons in a vapor-liquid wash. Generally, therefore, the liquid alcohol-containing stream used in the washing step comprises at least 75 wt % methanol and less than 25 wt % water, such as at least 80 wt % methanol and less than 20 wt % water, for example at least 98 wt % methanol and less than 2 wt % water, such as at least 99 wt % methanol and less than 1 wt % water.

In general, the temperature employed in the washing step should be no more than 130° F. (54° C.) so as to enhance the oxygenate adsorption capacity of the methanol and limit the amount of vaporized methanol exiting the vapor-liquid contacting device with the wash vapor stream. In addition, the temperature employed in the washing step is generally at least 34° F. (1° C.), so as to mitigate the potential for forming solids in the system. Conveniently, the temperature of the washing step is at least 70° F. (21° C.), so as to limit the amount of hydrocarbons adsorbed by the methanol to acceptable levels, such as at least 80° F. (27° C.), and no more than 120° F. (49° C.), for example no more than 110° F. (43° C.). Conveniently, the pressure at which the washing is conducted (also termed herein the "third" pressure) is less than 350 psig (2514 kPa), such as less than 200 psig (1480 kPa), for example less than 170 psig (1273 kPa), and greater than 100 psig (790 kPa), such as greater than 140 psig (1066 kPa).

Conveniently, the amount of methanol employed as the liquid alcohol-containing stream in the washing step is at least 0.03 lb (as pure methanol) per lb of the second effluent stream, or residual vapor effluent stream as appropriate, so as to ensure that there is sufficient methanol to (1) achieve a desired low level of $C_2$ to $C_6$ carbonyl compounds in the $C_4$ component of wash vapor effluent stream and (2) prevent the formation of a third, aqueous liquid phase in the vapor-liquid contacting device. In addition, the amount of methanol employed in the washing step is generally no more than 0.5 lb (as pure methanol) per lb of the second effluent stream, or residual vapor effluent stream, so as to limit the amount of $C_2$ to $C_4$ olefins absorbed into the wash liquid effluent stream. Preferably, the amount of methanol employed is as at least 0.05 lb, such as at least 0.06 lb, for example at least 0.07 lb methanol (as pure methanol) per lb of the second effluent stream or residual vapor effluent stream. In addition, the amount of methanol employed is preferably no more than 0.2 lb, such as no more than 0.15 lb, for example no more than 0.1 lb methanol (as pure methanol) per lb of the second effluent stream or residual vapor effluent stream.

Conveniently, the vapor-liquid contacting device used in the alcohol washing step is a countercurrent fractional distillation tower, in which the second effluent stream or residual vapor effluent stream is directed into the bottom of the tower and methanol is directed into the top of the tower. The wash vapor effluent stream exits the tower as overhead while the wash liquid effluent stream exits as a liquid bottoms stream.

The condensed liquid effluent stream (or streams) derived from the first vapor effluent stream in the compression/cooling stages, or the wash liquid effluent stream from the washing, contain $C_5+$ hydrocarbons, in addition to oxygenate species. The $C_5+$ hydrocarbons will typically comprise compounds that are at best unreactive in the OTO reaction, such as aromatics and saturated hydrocarbons. Thus, if these liquid effluent streams were recycled to the OTO reactor to utilize the oxygenates contained therein for the production of additional desired $C_2$ to $C_4$ olefins, for example either directly or via a water-oxygenate fractionation tower, they would carry these unreactive species with them. These unreactive species would pass through the OTO reactor largely intact, and over time build up to unacceptable levels in the streams moving within the reactor, quench, compression/cooling and wash equipment loop, which would detrimentally impact process efficiency and capacity. In the case of benzene, a build-up to certain concentrations in a given stream may provoke environmental and hygienic concerns that would require expensive means to mitigate.

Thus, in the method of the present invention, one or more of the liquid effluent streams are contacted with a liquid water-containing stream in a liquid-liquid contacting device, such as a liquid-liquid extraction column, so as to at least partially separate the given liquid effluent stream(s) into an aqueous phase rich in said one oxygenate species and an organic phase rich in said $C_5+$ hydrocarbons. When feeding the wash liquid effluent stream to the liquid-liquid contacting device, the organic phase will also be rich in the alcohol provided in the liquid alcohol-containing stream. This is particularly beneficial when both the primary oxygenate feed to the OTO reactor and the alcohol provided in the liquid alcohol-containing stream are methanol.

Conveniently, liquid-liquid contacting of the condensed liquid effluent stream(s) and/or the wash liquid effluent stream in the liquid-liquid contacting device is effected at a pressure of about atmospheric to about 600 psig (100 to 4238 kPa), such as about 5 to about 350 psig (135 to 2514 kPa) and a temperature of about 35 to about 210° F. (2 to 99° C.), such as about 70 to about 120° F. (21 to 49° C.), such as about 90 to about 110° F. (32 to 43° C.). In addition, the liquid-liquid contacting is conveniently effected by feeding the liquid water-containing stream to the liquid-liquid contacting device at a first rate and feeding the given liquid effluent stream to the device at a second rate, wherein the weight ratio of the second rate to the first rate ranges from about 0.1 to about 10, such as from about 0.2 to about 2, for example about 0.3 to about 1.4, such as about 0.6 to about 1.2. Where the oxygenate species in the pertinent liquid effluent stream includes methanol, the weight ratio of contained methanol in the second rate to the first rate ranges from about 0.1 to about 1, such as from about 0.2 to about 0.7, for example from about 0.3 to about 0.6. In general, the rate of liquid water-containing stream relative to the given liquid effluent stream should be high enough to educe the desired phases and extract the desired oxygenates into the aqueous phase, but not so high as to absorb a significant amount of C5+ hydrocarbons, particularly aromatics and saturates, into the aqueous phase merely through their natural solubility in water.

In one embodiment, the liquid-liquid contacting device used in the water washing step is a countercurrent extraction tower, in which the desired liquid effluent stream or streams are directed into the bottom of the tower and the liquid water-containing stream is directed into the top of the tower. The organic phase exits the tower as a liquid overhead product while the aqueous phase exits as a liquid bottoms product. Inside the extraction tower are devices to promote contacting between and separation of the two phases, such as perforated trays, or a number of some type of packing elements, such as Raschig rings, and potentially distribution elements such as grids, or dynamic mixing elements such as circulating blades.

The aqueous phase, now rich in oxygenate and largely depleted of unreactive species such as aromatics and saturates, can then be fed to the OTO reactor without the prospect of a build-up of unreactive species. In one embodiment, the aqueous phase can be fractionated to provide a water-rich fraction as a bottoms product and an overhead fraction rich in at least one oxygenate. For example, the aqueous phase can be fed to a water-oxygenate fractionation tower, taking advantage of its existence for processing water from the quench device, to allow the oxygenate species to be recovered as an overhead fraction which is rich in at least one oxygenate and which can be recycled to the OTO reactor. In another embodiment, at least a portion of the water-rich fraction derived from fractionation of the aqueous phase is used as at least a portion of the liquid water-containing stream for liquid-liquid contacting. Again, the aqueous phase may be fed to a water-oxygenate fractionation tower, and the liquid water-rich bottoms stream containing the water-rich fraction from the aqueous phase may be recycled for use in the liquid-liquid contacting.

The organic phase obtained from the liquid-liquid contacting can be used as fuel, for example to provide heat for the OTO plant. Alternatively, the organic phase can be further processed to recover material therein, for example, heavier oxygenates that may be found in the organic phase resulting from imperfect separation in the liquid water liquid contacting device (in general, the higher the molecular weight of an oxygenate, the more it behaves like a hydrocarbon in a liquid-liquid water contacting action and will exit with the organic phase).

A number of useful optional embodiments exist in the process of the present invention for providing the liquid effluent stream of choice to the liquid-liquid contacting device. For example, one or more liquid effluent streams, or portions thereof, can be provided to different liquid-liquid contacting devices to provide more than one aqueous phase and organic phase. Alternatively, one or more liquid effluent streams, or portions thereof, can be provided to a single liquid-liquid contacting device and provide a single aqueous phase and organic phase. It may be of benefit to mix two or more of the liquid effluent streams, or portions thereof, prior to introducing the mixture to the liquid-liquid contacting device.

In another embodiment, all or a portion of a liquid effluent stream may be exposed to one or more reductions in pressure to effect a vapor-liquid flash. For example, the condensed liquid effluent stream can be provided to a flash drum at a reduced pressure to produce a flash liquid effluent stream and a flash vapor effluent stream, or the wash liquid effluent stream can be provided to a flash drum at a reduced pressure to provide a wash flash liquid effluent stream and a wash flash vapor effluent stream. One or more of these flash liquid effluent streams, or portions thereof, or mixtures thereof, may then be provided for liquid-liquid contacting. Optionally, two or more liquid effluent streams may be provided to a common flash drum, for example a condensed liquid effluent stream and a wash liquid effluent stream, possibly having been mixed beforehand, to provide a common flash liquid effluent stream provided for liquid-liquid contacting. In a modified embodiment, all or a portion of a flash liquid effluent stream, or portions or combinations of flash liquid effluent streams may be subjected to an additional reduction in pressure to provide yet another flash liquid effluent stream to be provided for liquid-liquid contacting. Additional pressure reductions on subsequent flash liquid effluents may continue as desired.

This manifestation of the invention involving vapor-liquid flashes of liquid effluent streams may be useful in reducing the amount of lighter hydrocarbons, for example $C_2$ to $C_4$ olefins, present in the liquid effluent streams prior to the liquid-liquid contacting, thus potentially increasing their eventual recovery. Thus, in another embodiment of the invention, the flash vapor effluent generated by exposing a liquid effluent stream, or portions or combinations thereof, to a reduction in pressure is recycled along with another vapor effluent stream, for example the first vapor effluent stream or the first residual vapor stream depending on the flash conditions and compressor suction pressures, to a stage of compression and cooling. In this manner, for example, the desired $C_2$ to $C_4$ olefins will build up in the streams in the compression/cooling and flash equipment loop until they emerge with a residual vapor effluent stream, or the wash vapor effluent stream, for further processing and recovery.

The invention will now be more particularly described with reference to the accompanying drawings.

Referring to FIG. 1, there is illustrated therein a process for converting an oxygenate to olefins according to a first example of the invention. An oxygenate feedstock, for example, methanol, is provided in line 10 to oxygenate to olefin reactor 12 for conversion to a vapor product stream comprising $C_2$ to $C_4$ olefins, $C_5$+ hydrocarbons, unreacted methanol and water, which exits the oxygenate to olefin reactor 12 in line 14 at a reaction pressure.

The vapor product stream in line 14 is provided to a cooling device, in this instance a quench tower 16. The cooling in quench tower 16 serves to condense from the vapor product stream in line 14 a liquid water-rich bottoms stream in line 20 near the bottom of quench tower 16, and also provide, from near the top of quench tower 16, a first vapor effluent stream in line 18 at an initial pressure that is no greater than the reaction pressure, and further that comprises no more than 10 wt. % water.

The first vapor effluent stream in line 18 is provided to the suction of a compressor 22 at a first suction pressure that is no greater than the reaction pressure. The vapor product stream in line 18 is compressed in compressor 22 to produce a compressed first vapor effluent stream in line 24 that is at a second pressure greater than the first suction pressure. The second vapor effluent stream in line 24 is then cooled in cooling device, in this instance a shell and tube heat exchanger 26, with the entrance and exit of a cooling fluid denoted by the unnumbered lines. The cooling of the compressed first vapor effluent stream in line 24 through heat exchanger 26 serves to produce a second effluent stream in line 28 that is partially in the vapor state. The second effluent stream in line 28 is directed to flash drum 30 to effect the separation of the second effluent stream into a condensed liquid effluent stream in line 34 comprising $C_5$+ hydrocarbons and unreacted methanol and a residual vapor effluent stream in line 32 comprising $C_2$ to $C_4$ olefins. The residual vapor effluent stream in line 32 is suitable for further processing to recover and purify the various olefins.

The condensed liquid effluent stream in line 34 is provided to liquid-liquid contacting device 36, in this instance a liquid-liquid extraction tower, at a point near the bottom of the extraction tower 36. A liquid water-containing stream in line 38 is also provided to a point near the top of extraction tower 36, and the contacting that occurs therein effects a separation of $C_5+$ hydrocarbons from the condensed liquid effluent stream in line 34 into an organic phase exiting in line 40 from near the top of extraction tower 36 (the hydrocarbons in the organic phase within extraction tower 36 are less dense than the water within extraction tower 36, and hence tend to rise). Further, the water from the liquid water-containing stream in line 38 that is within extraction tower 36 stream will absorb the methanol, and substantial quantities of many other oxygenates that may be present from the condensed liquid effluent stream in line 34, into an aqueous phase in line 42 from near the bottom of extraction tower 36 (the water in the aqueous phase within extraction tower 36 is more dense than the hydrocarbons within extraction tower 36, and thus tends to fall).

Figure 2:
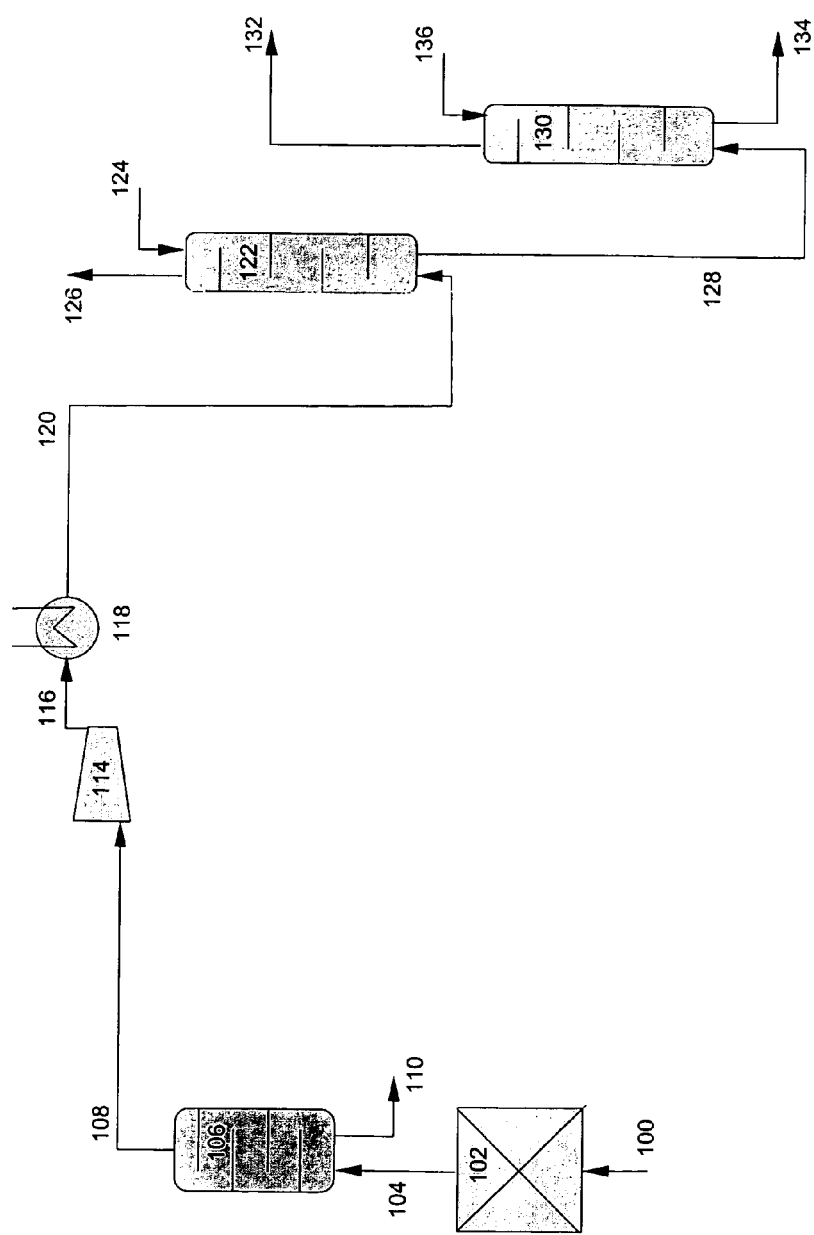
FIG. 2 is a schematic flow diagram illustrating a process according to a second example of the invention.

Directing attention to FIG. 2, there is illustrated therein a process for converting an oxygenate to olefins according to a second example of the invention. An oxygenate feedstock, for example, methanol, is provided in line 100 to oxygenate to olefin reactor 102 for conversion to a vapor product stream comprising $C_2$ to $C_4$ olefins, $C_5+$ hydrocarbons, $C_2$ to $C_6$ carbonyl compounds, unreacted methanol and water, which exits the oxygenate to olefin reactor 102 in line 104 at a reaction pressure.

The vapor product stream in line 104 is provided to a cooling device, in this instance a quench tower 106. The cooling in quench tower 106 serves to condense from the vapor product stream in line 104 a liquid water-rich bottoms stream in line 110 near the bottom of quench tower 106, and also provide, from near the top of quench tower 106, a first vapor effluent stream in line 108 at an initial pressure that is no greater than the reaction pressure, and further that comprises no more than 5 wt. % water.

The first vapor effluent stream in line 108 is provided to the suction of a compressor 114 at a first suction pressure that is no greater than the initial pressure. The vapor product stream in line 108 is compressed in compressor 114 to produce a compressed first vapor effluent stream in line 116 that is at a second pressure greater than the first suction pressure. The second vapor effluent stream in line 116 is then cooled in cooling device, in this instance a shell and tube heat exchanger 118, to produce a second effluent stream in line 120 that is at least partially in the vapor state.

The second effluent stream is communicated via line 120 to a vapor-liquid contacting device, in this case absorber fractionation tower 122, at a point near the bottom of the absorber tower 122 to allow the vapor portion of the second effluent stream to rise through the contacting device. An alcohol wash is effected in absorber tower 122 by providing a liquid alcohol-containing stream, in this case methanol, in line 124 to a point near the top of the absorber tower 122. Conveniently, the pressure in absorber tower 122 is greater than the first suction pressure but no greater than the second pressure.

The liquid methanol-containing stream in line 124 will flow down through the absorber tower 122, contacting the second effluent stream, preferentially absorbing $C_2$ to $C_6$ carbonyl compounds, and also absorbing a significant amount of $C_5+$ hydrocarbons, thus producing a wash liquid stream in line 128 from near the bottoms of absorber tower 122. From near the top of absorber tower 122, a wash vapor stream is produced in line 126 that has a lower content of $C_2$ to $C_6$ carbonyl compounds than the first vapor effluent stream in line 108, suitable for further processing to recover and purify the various olefins. It is likely that the wash vapor stream in line 126 will further comprise some of the methanol contained in the liquid methanol-containing stream in line 124.

The wash liquid effluent stream in line 128 is provided to liquid-liquid contacting device 130, in this instance a liquid-liquid extraction tower, at a point near the bottom of the extraction tower 130. A liquid water-containing stream in line 136 is also provided to a point near the top of extraction tower 130, and the contacting that occurs therein effects a separation of $C_5+$ hydrocarbons from the wash liquid effluent stream in line 128 into an organic phase exiting in line 132 from near the top of extraction tower 130. Further, the water from the liquid water-containing stream in line 136 that is within extraction tower 130 stream will absorb the methanol (both the unreacted methanol from the vapor product stream in line 108 and the methanol from the liquid alcohol-containing stream in line 124), and substantial quantities of many other oxygenates that may be present from the condensed liquid effluent stream in line 128, into an aqueous phase in line 134 from near the bottom of extraction tower 130.

Figure 3:
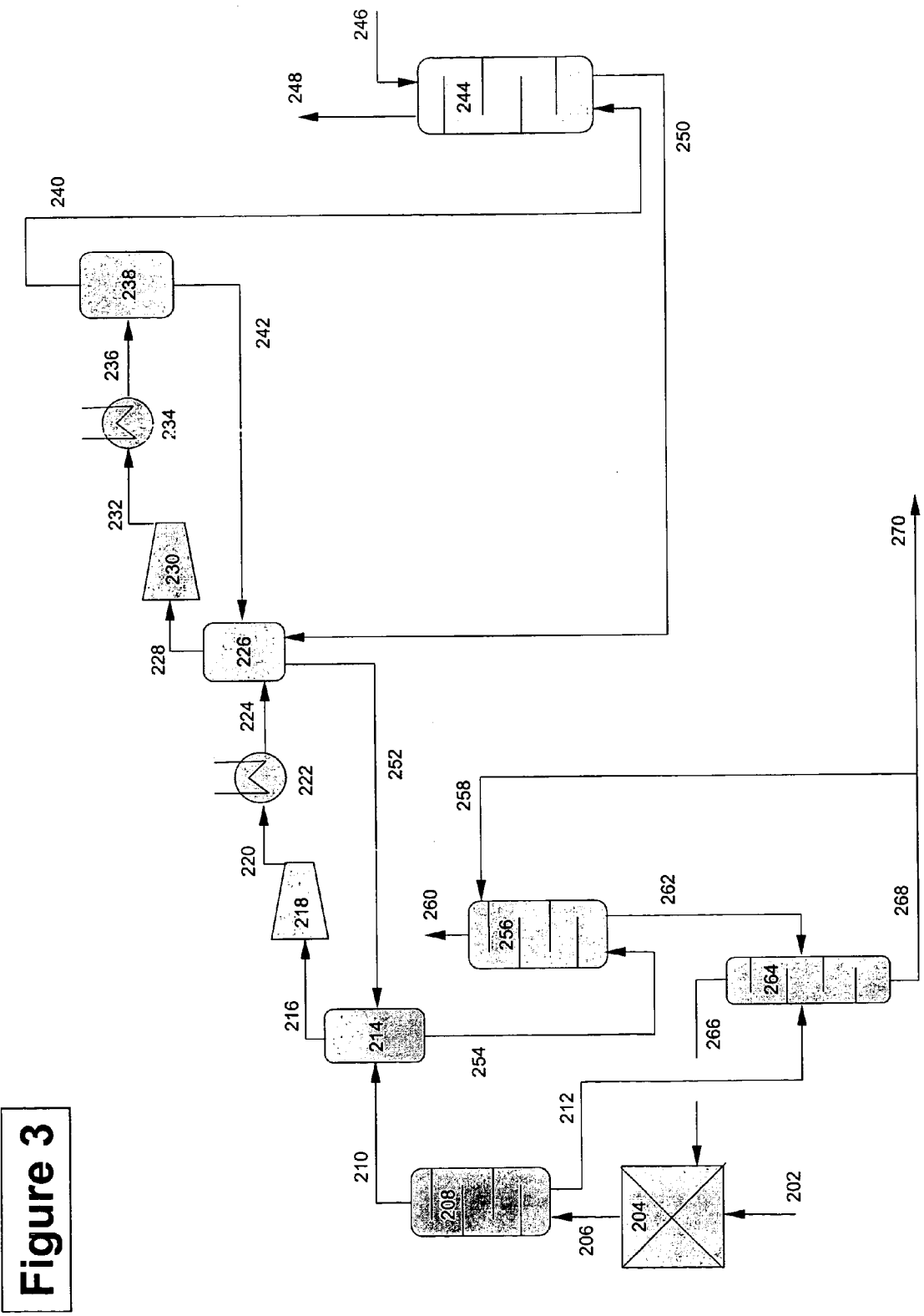
FIG. 3 is a schematic flow diagram illustrating a process according to a third example of the invention.

Now with regard to FIG. 3, there is illustrated therein a process for converting an oxygenate to olefins according to a third example of the invention. An oxygenate feedstock, for example methanol, is provided in line 202, along with a fraction rich in at least one oxygenate, again for example containing methanol, in line 266, to oxygenate to olefin reactor 204. The methanol and any other oxygenates are converted to a vapor product stream comprising $C_2$ to $C_4$ olefins, $C_5+$ hydrocarbons, unreacted methanol and water, which exits the oxygenate to olefin reactor 204 in line 206 at a reaction pressure.

The vapor product stream in line 206 is provided to a cooling device, in this instance a quench tower 208. The cooling in quench tower 208 serves to condense from the vapor product stream in line 206 a liquid water-rich bottoms stream in line 212 near bottom of quench tower 208, and also provide, from near the top of quench tower 208, a first vapor effluent stream in line 210 at an initial pressure that is no greater than the reaction pressure, and further that comprises no more than 2 wt. % water.

The first vapor effluent stream in line 210 is fed, via a flash drum 214, and line 216, to the suction of a compressor 218 at a first suction pressure that is no greater than the initial pressure. The flash drum 214 also receives a common first condensed liquid effluent stream, first flash liquid effluent stream and first wash flash liquid effluent stream through line 252, and exposes this common stream in line 252 to a pressure of at least the first suction pressure and less than an intermediate pressure to produce a second flash vapor effluent stream and second wash flash vapor effluent stream, and a second flash liquid effluent stream and second wash flash liquid effluent stream. The second flash vapor effluent stream and second wash flash vapor effluent stream exit the drum 214 through line 216, as a common stream with the first vapor effluent stream in line 216, to the suction of compressor 218. The second flash liquid effluent stream and second wash flash liquid effluent stream exit the drum 214 as a common stream through line 254, and carry with them at least part of the unreacted methanol and $C_2$ to $C_6$ carbonyl compounds from the first vapor effluent stream in line 210.

The common stream in line 216 is compressed in compressor 218 to produce a compressed first vapor effluent stream in line 220 that is at an intermediate pressure greater than the initial pressure. The compressed first vapor effluent stream in line 220 is then cooled in a cooling device, in this instance a shell and tube heat exchanger 222. The cooling of the compressed first vapor effluent stream in line 220 through heat exchanger 222 serves to produce a compressed and cooled first vapor effluent stream in line 224 (also termed herein a first "condensate") that is partially in the vapor state. The first condensate is fed by line 224 to a another flash drum 226, where the first condensate is separated into a first residual effluent vapor stream in line 228 and the common first condensed liquid effluent stream, first flash liquid effluent stream and first wash flash liquid effluent stream in line 252. The first residual effluent vapor stream in line 228 is communicated to the suction of another compressor 230 at an intermediate suction pressure that is no greater than the intermediate pressure.

The second flash drum 226 also receives a second condensed liquid effluent stream through line 242 and a wash liquid stream through line 250. In drum 226, the second condensed liquid effluent stream and the wash liquid stream are exposed to a pressure of at least the intermediate suction pressure and less than a third pressure to produce a first flash vapor effluent stream and first wash flash vapor effluent stream, and a first flash liquid effluent stream and first wash flash liquid stream. The first flash vapor effluent stream and first wash flash vapor effluent stream exit the drum 226 through line 228, as a common stream with the first remaining vapor effluent vapor stream, to the suction of compressor 230. Further, the first flash liquid effluent stream and first wash flash liquid streams exit the drum 226 through line 252, as a common stream with the first condensed liquid effluent stream and are returned to the first flash drum 214.

The common stream in line 228 is compressed in compressor 230 to produce a compressed first residual vapor effluent stream in line 232 that is at a second pressure greater than the intermediate pressure. The compressed first residual vapor effluent stream in line 232 is then cooled in cooling device, in this example another shell and tube heat exchanger 234, to produce a second effluent stream in line 236 that is partially in the vapor state. The second effluent stream in line 236 is fed to yet another flash drum 238, to form the second condensed liquid effluent stream in line 242 and a second residual vapor effluent stream in line 240 from near the top of flash drum 238.

The second residual vapor effluent stream is communicated via line 240 to a vapor-liquid contacting device, in this case absorber fractionation tower 244, at a point near the bottom of the absorber tower 244. An alcohol wash is effected at the third pressure, greater than the intermediate suction pressure but not greater than the second pressure, in absorber tower 244 by providing a liquid alcohol-containing stream, in this case containing methanol, in line 246 at a point near the top of the absorber tower 244. The liquid methanol-containing stream in line 246 flows down through the absorber tower 244, contacting the second residual vapor effluent stream, preferentially absorbing $C_2$ to $C_6$ carbonyl compounds, and also absorbing $C_5+$ hydrocarbons, and some $C_2$ to $C_4$ olefins, thus producing the wash liquid stream in line 250 from near the bottoms of absorber tower 244. From near the top of absorber tower 244, a wash vapor stream is produced in line 248 that has a lower content of $C_2$ to $C_6$ carbonyl compounds and $C_5+$ hydrocarbons than the first vapor effluent stream in line 210, suitable for further processing to recover and purify the various olefins. It is likely that the wash vapor stream in line 248 will further comprise some of the methanol contained in the liquid alcohol-containing stream in line 246.

The common second flash liquid effluent stream and second wash flash liquid effluent stream in line 254 is provided to liquid-liquid contacting device 256, in this instance a liquid-liquid extraction tower, at a point near the bottom of the extraction tower 256. A liquid water-containing stream in line 258 is also provided to a point near the top of extraction tower 256, and the contacting that occurs therein effects a separation of $C_5+$ hydrocarbons from the common liquid effluent stream in line 254 into an organic phase exiting in line 260 from near the top of extraction tower 256. Further, the water from the liquid water-containing stream in line 258 that is within extraction tower 256 stream will absorb the methanol (both the unreacted methanol from the vapor product stream in line 210 and the methanol from the liquid alcohol-containing stream in line 246), and quantities of the $C_2$ to $C_6$ carbonyls that may be present from the common liquid effluent stream in line 254, into an aqueous phase in line 262 from near the bottom of extraction tower 256.

Both the liquid water-rich bottoms stream in line 212 and the aqueous phase in line 262 are fed to a water-oxygenate fractionation tower 264 that separates them into the overhead product fraction rich in at least one oxygenate in line 266 and a substantially pure water as a bottoms stream in line 268. The overhead product fraction rich in at least one oxygenate in line 266 is recycled as feed to the oxygenate to olefin reactor 204. A portion of the substantially pure water stream in line 268 is used as the liquid water-containing stream in line 258 in extraction tower 256, and the balance of the substantially pure water stream is directed elsewhere in line 270.

In an optional embodiment, the wash vapor effluent stream is subjected to a second washing step in which the wash vapor effluent stream is washed with water in a second vapor-liquid contacting device, again typically a countercurrent fractional distillation tower, to produce a water-washed vapor effluent stream and an water wash liquid bottoms stream. Conveniently, the water employed in the second washing step is the substantially pure water bottoms stream obtained from the water-oxygenate fractionation tower. Moreover, the water wash liquid bottoms stream from the second washing step is conveniently returned to the water-oxygenate fractionation tower to allow recovery and recycle of the water to the second washing step.

In general, the temperature employed in the second washing step should be no more than 120° F. (49° C.) so as to enhance the oxygenate adsorption capacity of the water and limit the amount of water vapor exiting the second vapor-liquid contacting device with the water-washed vapor effluent stream. Conveniently, the temperature of the second washing step is at least 70° F. (21° C.), for example at least 80° F. (27° C.), such as at least 90° F., and no more than 110° F. (43° C.), for example no more than 100° F. (38° C.). Conveniently, the second washing step is conducted at or near said third pressure.

Conveniently, said water-washed vapor effluent stream comprises less than 0.5 wt. %, such as less than 0.1 wt %, for example less than 500 ppmwt, of $C_2$ to $C_6$ carbonyl compounds based on the total weight of water-washed vapor effluent stream. In addition, the water-washed vapor effluent stream conveniently comprises less than 1.0 wt. %, such as less than 0.1 wt %, for example less than 500 ppmwt, of methanol based on the total weight of water-washed vapor effluent stream. The water-washed vapor effluent stream can then be processed to recover the $C_2$ to $C_4$ olefins and higher hydrocarbons present in this stream.

In one embodiment of such a recovery process, at least part of the water-washed vapor effluent stream is contacted with a basic component, such as caustic or an amine, to remove the bulk of the carbon dioxide therefrom, whereafter the $CO_2$-depleted stream is dried, for example in a molecular sieve drier, so that the dried effluent stream has a dew point no greater than −150° F. (−101° C.), such as no greater than −200° F. (−129° C.). At least part of the dried effluent stream is then fractionated to produce a $C_3$ and $C_3$-containing overhead stream and a $C_4$+ containing bottoms stream. The $C_3$ and $C_3$-containing overhead can then be processed in conventional manner to separate the ethylene and propylene product fractions.

The invention will now be more particularly described with reference to the following practical example of the process shown in FIG. 1.

EXAMPLE

A pilot plant trial of the process shown in FIG. 2 was conducted in which the second effluent stream was washed in the absorber fractionation tower 122 at a pressure of 150 psig (1135 kPa) and a methanol flow rate of 15 lb/hour. The composition of the second vapor effluent stream in line 116 and the wash vapor stream in line 126 are shown below in Table 1.

TABLE 1

| Component | Second Effluent Stream (wt %) | Wash Vapor Stream (wt %) | % Change |
|---|---|---|---|
| Dimethyl ether | 3.7661 | 2.7718 | −26.4015 |
| Methyl ethyl ether | 0.0101 | 0.0000 | −100.0000 |
| Methyl isopropyl ether | 0.0007 | 0.0000 | −100.0000 |
| Acetaldehyde | 0.0417 | 0.0378 | −9.5362 |
| 2-Methoxy butane | 0.0002 | 0.0000 | −100.0000 |
| Propanal | 0.0111 | 0.0000 | −100.0000 |
| Acrolein | 0.0001 | 0.0000 | −100.0000 |
| Methacrolein | 0.0036 | 0.0000 | −100.0000 |
| Unknown | 0.0003 | 0.0000 | −100.0000 |
| Butanal | 0.0032 | 0.0000 | −100.0000 |
| Methyl acetate | 0.0002 | 0.0000 | −100.0000 |
| Methanol | 2.7353 | 2.3179 | −15.2629 |
| Acetone | 0.1601 | 0.0813 | −49.2466 |
| Isovaleraldehyde | 0.0003 | 0.0000 | −100.0000 |
| Dimethylacetal | 0.0020 | 0.0000 | −100.0000 |
| Pentanal | 0.0005 | 0.0000 | −100.0000 |
| 2-Butanone | 0.0375 | 0.0000 | −100.0000 |
| Ethanol | 0.0008 | 0.0000 | −100.0000 |
| 3-Methyl-3-buten-2-one | 0.0014 | 0.0000 | −100.0000 |
| Unknown | 0.0002 | 0.0000 | −100.0000 |
| Crotonaldehyde | 0.0002 | 0.0000 | −100.0000 |
| 3-Methyl-2-butanone | 0.0042 | 0.0000 | −100.0000 |
| 3-Pentanone | 0.0021 | 0.0000 | −100.0000 |
| 2-Methyl butanol | 0.0002 | 0.0000 | −100.0000 |
| 2-Pentanone | 0.0022 | 0.0000 | −100.0000 |
| 3-Butenol | 0.0003 | 0.0000 | −100.0000 |
| 3-Methyl-2-pentanone | 0.0003 | 0.0514 | 19009.5609 |
| t-Butanol | 0.0001 | 0.0000 | −100.0000 |
| Methane | 1.2653 | 1.2563 | 0.0000 |
| Ethane | 0.5437 | 0.5308 | −2.3655 |
| Ethylene | 30.6933 | 29.9435 | −2.4430 |
| Propane | 0.9249 | 0.7663 | −17.1554 |
| Cyclopropane | 0.0031 | 0.0000 | −100.0000 |
| Propylene | 35.4988 | 31.0685 | −12.4804 |
| Isobutane | 0.0849 | 0.0587 | −30.8560 |
| n-Butane | 0.2579 | 0.1672 | −35.1748 |
| Methyl cyclopropane | 0.0039 | 0.0000 | −100.0000 |

TABLE 1-continued

| Component | Second Effluent Stream (wt %) | Wash Vapor Stream (wt %) | % Change |
|---|---|---|---|
| Trans-2-Butene | 5.1322 | 3.6158 | −29.5467 |
| 1-Butene | 3.3856 | 2.5235 | −25.4634 |
| Iso-Butene | 0.7129 | 0.5469 | −23.2929 |
| Cis-2-Butene | 3.8081 | 2.6364 | −30.7689 |
| Isopentane | 0.0043 | 0.0349 | 706.3496 |
| 1,2-Butadiene | 0.0561 | 0.0000 | −100.0000 |
| Pentane | 0.0581 | 0.0000 | −100.0000 |
| Methyl acetylene | 0.0022 | 0.0000 | −100.0000 |
| 1.3-Butadiene | 0.4457 | 0.0280 | −93.7131 |
| C5+ | 10.3408 | 4.0294 | −61.0339 |
| H2O/CO/CO2 | 0.0000 | 0.1403 | Undefined |

It will be seen from Table 1 that the methanol wash removes many of the oxygenates in the second vapor effluent stream, except for part of the dimethyl ether, acetaldehyde, acetone and 3-methyl-pentanone. However, it will be seen that the methanol wash step also removes non-negligible amounts of ethylene and propylene product, and substantial amounts of $C_5$+ hydrocarbons, which are managed advantageously in the method of the present invention.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A process for producing olefins comprising:
   (a) providing a vapor product stream from an oxygenate to olefin conversion reaction comprising $C_2$ to $C_4$ olefins, $C_5$+ hydrocarbons, at least one oxygenate and water;
   (b) cooling the vapor product stream to remove water therefrom and produce a first vapor effluent stream;
   (c) compressing and cooling the first vapor effluent stream to produce a condensed liquid effluent stream comprising $C_5$+ hydrocarbons and at least one oxygenate, and a residual vapor effluent stream comprising $C_2$ to $C_4$ olefins; and
   (d) contacting at least a portion of the condensed liquid effluent steam with a liquid water-containing stream in a liquid-liquid contacting device to at least partly separate said condensed liquid effluent stream, or portion thereof, into an aqueous phase rich in said at least one oxygenate and an organic phase rich in said $C_5$+ hydrocarbons.

2. The process of claim 1 wherein said at least one oxygenate includes methanol.

3. The process of claim 2 wherein said vapor product stream in (a) comprises from about 1 wt. % to about 10 wt. % methanol.

4. The process of claim 1 wherein the first vapor effluent stream produced in (b) has a pressure ranging from about 108 kPaa (1 psig) to about 1480 kPaa (200 psig).

5. The process of claim 1 wherein the first vapor effluent stream produced in (b) has a pressure ranging from about 108 kPaa (1 psig) to about 791 kPaa (100 psig).

6. The process of claim 1 wherein the first vapor effluent stream produced in (b) has a pressure ranging from about 136 kPaa (5 psig) to about 377 kPaa (40 psig).

7. The process of claim 1 wherein the first vapor effluent stream produced in (b) has a temperature ranging from about 20° C. (68° F.) to about 54° C. (130° F.).

8. The process of claim 1 wherein the first vapor effluent stream produced in (b) has a temperature ranging from about about 32° C. (90° F.) to about 43° C. (110° F.).

9. The process of claim 1 wherein the condensed liquid effluent stream and the residual vapor effluent stream produced in (c) have a pressure ranging from about 446 kPaa (50 psig) to about 2514 kPaa (350 psig).

10. The process of claim 1 wherein the coudensed liquid effluent stream and the residual vapor effluent stream produced in (c) have a pressure ranging fran, about 791 kPaa (100 psig) to about 2100 kPaa (290 psig).

11. The process of claim 1 wherein the condensed liquid effluent stream and the residual vapor effluent stream produced in (c) have a pressure ranging from about 1066 kPaa (140 psig) to about 1342 kPaa (180 psig).

12. The process of claim 1 wherein the condensed liquid effluent stream produced in (c) comprises up to about 20 wt. % aromatics.

13. The process of claim 1 wherein the condensed liquid effluent stream produced in (c) comprises up to about 10 wt. % aromatics.

14. The process of claim 1 wherein the condensed liquid effluent stream produced in (c) comprises up to about 1 wt. % aromatics.

15. The process of claim 1 wherein the condensed liquid effluent stream produced in (c) comprises up to about 10 wt. % benzene.

16. The process of claim 1 wherein the condensed liquid effluent stream produced in (c) comprises up to about 5 wt. % benzene.

17. The process of claim 1 wherein the condensed liquid effluent stream produced in (c) comprises up to about 0.5 wt. % benzene.

18. The process of claim 1 wherein the condensed liquid effluent stream produced in (c) comprises at least about 1 wt. % of said at least one oxygenate.

19. The process of claim 1 wherein the condensed liquid effluent stream produced in (a) comprises at least about 10 wt. % of said at least one oxygenate.

20. The process of claim 1 wherein the condensed liquid effluent stream produced in (c) comprises at least about 20 wt. % of said at least one oxygenate.

21. The process of claim 1 wherein the vapor product stream in (a) further comprises $C_2$ to $C_6$ carbonyls, and the condensed liquid effluent stream produced in (c) comprises at least 0.10 wt. % $C_2$ to $C_6$ carbonyls.

22. The process of claim 1 wherein the vapor product steam in (a) further comprises $C_2$ to $C_6$ carbonyls, and the condensed liquid effluent stream produced in (c) comprises at least 5 wt. % $C_2$ to $C_6$ carbonyls.

23. The process of claim 1 wherein the vapor product stream in (a) further comprises $C_2$ to $C_6$ carbonyls, and the condensed liquid effluent stream produced in (c) comprises at least 10 wt. % $C_2$ to $C_6$ carbonyls.

24. The process of claim 1 wherein (c) comprises compressing the first vapor affluent stream, cooling the compressed first vapor effluent stream to form a condensate and providing the condensate to a vessel to separate the condensed liquid effluent stream from the residual vapor effluent stream.

25. The process of claim 1 wherein (c) comprises compressing the first vapor effluent stream; cooling the compressed first vapor effluent stream to produce a first condensed liquid effluent steam and a first residual vapor effluent stream; compressing the first residual vapor effluent stream and cooling the compressed first residual vapor effluent stream to produce a second condensed liquid effluent stream and a second residual vapor effluent stream and, further wherein at least a portion of the condensed liquid effluent stream in (d) is selected from the group consisting of the first condensed liquid effluent stream, the second condensed liquid effluent stream and mixtures thereof.

26. The process of claim 1 wherein the liquid water-containing stream in (d) comprises at least 90 wt. % water.

27. The process of claim 1 wherein the liquid water-containing stream in (d) comprises at least 95 wt. % water.

28. The process of claim 1 wherein said organic phase in (d) comprises up to about 95 wt. % $C_5$+ hydrocarbons.

29. The process of claim 1 wherein said organic phase in (d) comprises up to about 75 wt. % $C_5$+ hydrocarbons.

30. The process of claim 1 wherein said organic phase in (d) comprises up to about 40 wt. % $C_2$ to $C_6$ carbonyls.

31. The process of claim 1 wherein said organic phase in (d) comprises up to about 25 wt. % $C_2$ to $C_6$ carbonyls.

32. The process of claim 1 wherein said contacting (d) is conducted within said liquid-liquid contacting device at a pressure of from about 170 kPaa (10 psig) to about 2514 kPaa (350 psig), and a temperature of from about 1° C. (34° F.) to about 54° C. (130° F.).

33. The process of claim 1 wherein said contacting (d) is conducted within said liquid-liquid contacting device at a pressure of from about 446 kPaa (50 psig) to about 1480 kPaa (200 psig), and a temperature of from about 21° C. (70° F.) to about 43° C. (110° F.).

34. The process of claim 1 wherein the contacting (d) comprises feeding the liquid water-containing stream to the liquid-liquid contacting device at a first rate and feeding the condensed liquid effluent stream to the liquid-liquid contacting device at a second rate, wherein the weight ratio of the second rate to the first rate ranges from about 0.1 to about 10.

35. The process of claim 34 wherein the weight ratio of the second rate to the first rate ranges from about 0.2 to about 2.

36. The process of claim 34 wherein the weight ratio of the second rate to the first rate ranges from about 0.3 to about 1.4.

37. The process of claim 34 wherein the weight ratio of the second rate to the first rate ranges from about 0.6 to about 1.2.

38. The process of claim 34 wherein said at least one oxygenated hydrocarbon includes methanol and the weight ratio of methanol in the second rate to the first rate ranges from about 0.1 to about 1.

39. The process of claim 38 wherein the weight ratio of methanol in the second rate to the first rate ranges from about 0.2 to about 0.7.

40. The process of claim 38 wherein the weight ratio of methanol in the second rate to the first rate ranges from about 0.3 to about 0.6.

41. The process of claim 1 further comprising fractionating the aqueous phase into a water-rich fraction and a fraction rich in said at least one oxygenate.

42. The process of claim 41 wherein at least a portion of said liquid water-containing stream in (d) is at least a portion of said water-rich fraction.

43. The process of claim 41 wherein at least part of said fraction rich in said at least one oxygenate is recycled to said oxygenate to olefin conversion reaction.

44. The process of claim 1 further comprising exposing said condensed liquid effluent stream produced in (c) to one or more reductions in pressure to form a flash liquid effluent stream, wherein said flash liquid effluent stream is provided as the portion of the condensed liquid effluent stream for contacting (d).

45. The process of claim 44 wherein the flash liquid effluent stream comprises up to about 20 wt. % aromatics.

46. A process for producing olefins comprising:
(a) providing a vapor product stream from an oxygenate to olefin reaction comprising $C_2$ to $C_4$ olefins, $C_5+$ hydrocarbons, at least one oxygenate and water;
(b) cooling the vapor product stream to remove water therefrom and produce a first vapor effluent stream;
(c) compressing and cooling the first vapor effluent stream to produce a second effluent stream that is at least partially in the vapor state;
(d) washing at least part of the second effluent stream with a liquid alcohol-containing stream to remove at least a portion of at least one oxygenate from the second effluent stream in a wash liquid effluent stream, and produce a wash vapor effluent stream comprising $C_2$ to $C_4$ olefins, the wash liquid effluent stream further comprising $C_5+$ hydrocarbons and alcohol contained in the liquid alcohol-containing stream; and
(e) contacting at least a portion of the wash liquid effluent steam with a liquid water-containing stream in a liquid-liquid contacting device to at least partially separate said wash liquid effluent stream, or portion thereof, into an aqueous phase rich in said at least one oxygenate and alcohol from the liquid alcohol-containing stream, and an organic phase rich in said $C_5+$ hydrocarbons.

47. The process of claim 46 wherein said liquid alcohol-containing stream comprises at least one alcohol from the group consisting of methanol and ethanol.

48. The process of claim 46 wherein said liquid alcohol-containing stream comprises methanol.

49. The process of claim 46 wherein the wash liquid effluent stream produced in (d) comprises up to about 20 wt. % aromatics.

50. The process of claim 46 wherein the wash liquid effluent stream produced in (d) comprises up to about 10 wt. % aromatics.

51. The process of claim 46 wherein the wash liquid effluent stream produced in (d) comprises up to about 1 wt. % aromatics.

52. The process of claim 46 wherein the wash liquid effluent stream produced in (d) comprises at least about 1 wt. % of said at least one oxygenate.

53. The process of claim 46 wherein the wash liquid effluent stream produced in (d) comprises at least about 10 wt. % of said at least one oxygenate.

54. The process of claim 46 wherein the wash liquid effluent stream produced in (d) comprises at least about 20 wt. % of said at least one oxygenate.

55. The process of claim 46 wherein the wash liquid effluent stream produced in (d) comprises at least about 10 wt. % alcohol contained in the liquid alcohol-containing stream.

56. The process of claim 46 wherein the wash liquid effluent stream produced in (d) comprises at least about 20 wt. % alcohol contained in the liquid alcohol-containing stream.

57. The process of claim 46 wherein the liquid water-containing stream in (e) comprises at least 90 wt. % water.

58. The process of claim 46 wherein the liquid water-containing stream in (e) comprises at least 95 wt. % water.

59. The process of claim 46 wherein said organic phase in (e) comprises up to about 95 wt. % $C_5+$ hydrocarbons.

60. The process of claim 46 wherein said organic phase in (e) comprises up to about 75 wt. % $C_5+$ hydrocarbons.

61. The process of claim 46 wherein said organic phase in (e) comprises up to about 40 wt. % $C_2$ to $C_6$ carbonyls.

62. The process of claim 46 wherein said organic phase in (e) comprises up to about 25 wt. % $C_2$ to $C_6$ carbonyls.

63. The process of claim 46 wherein said contacting (e) is conducted at a pressure of from about 170 kPaa (10 psig) to about 2514 kPaa (350 psig), and a temperature of from about 1° C. (34° F.) to about 54° C. (130° F.).

64. The process of claim 46 wherein said contacting (e) is conducted within said liquid-liquid contacting device at a pressure of from about 446 kPaa (50 psig) to about 1480 kPaa (200 psig), and a temperature of from about 21° C. (70° F.) to about 43° C. (110° F.).

65. The process of claim 46 further comprising exposing said wash liquid effluent stream produced in (d) to one or more reductions in pressure to form a wash flash liquid effluent stream, wherein said wash flash liquid effluent stream is provided as the portion of the wash liquid effluent stream for contacting (e).

66. The process of claim 65 wherein the wash flash liquid effluent stream comprises up to about 20 wt. % aromatics.

67. The process of claim 65 wherein the wash flash liquid effluent stream comprises at least about 30 wt. % alcohol contained in the liquid alcohol-containing stream.

68. The process of claim 46 wherein (c) comprises compressing the first vapor effluent stream; cooling the compressed first vapor effluent stream to produce a first condensed liquid effluent stream and a first residual vapor effluent stream; compressing the first residual vapor effluent stream; and cooling the compressed first residual vapor effluent stream to produce a second residual vapor effluent stream that is at least partially in the vapor state, said second residual vapor effluent stream being provided for said washing (d).

69. The process of claim 46 further comprising fractionating the aqueous phase into a water-rich fraction and a fraction rich in said at least one oxygenate.

70. The process of claim 46 wherein at least a portion of said liquid water-containing stream in (e) is at least a portion of said water-rich fraction.

71. A process for producing olefins comprising:
(a) providing a vapor product stream from an oxygenate to olefin reaction comprising $C_2$ to $C_4$ olefins, $C_5+$ hydrocarbons, at least one oxygenate and water;
(b) cooling the vapor product stream to remove water therefrom and produce a first vapor effluent stream;
(c) compressing and cooling the first vapor effluent stream to produce a condensed liquid effluent stream comprising $C_5+$ hydrocarbons and at least one oxygenate, and a residual vapor effluent steam comprising $C_2$ to $C_4$ olefins, and;
(d) washing at least part of the residual vapor effluent stream with a liquid alcohol-containing stream to produce a wash vapor effluent stream comprising $C_2$ to $C_4$ olefins, and a wash liquid effluent stream comprising said at least one oxygenated hydrocarbon and said $C_5+$ hydrocarbons; and
(e) contacting at least a portion of the condensed liquid effluent stream produced in (c) and at least a portion of the wash liquid effluent stream produced in (d) with a liquid water-containing stream in a liquid-liquid contacting device to at least partially separate said condensed liquid effluent stream produced in (c) and the wash liquid effluent stream produced in (d), or portions thereof; into an aqueous phase rich in said at least one oxygenate and alcohol contained in the liquid alcohol containing stream, and an organic phase rich in said $C_5+$ hydrocarbons.

72. The process of claim 71 wherein said liquid alcohol-containing stream comprises methanol and/or ethanol.

73. The process of claim 71 wherein said liquid alcohol-containing stream comprises methanol.

74. The process of claim 71 wherein the wash liquid effluent stream produced in (d) comprises up to about 20 wt. % aromatics.

75. The process of claim 71 wherein the wash liquid effluent stream produced in (d) comprises up to about 10 wt. % aromatics.

76. The process of claim 71 wherein the wash liquid effluent stream produced in (d) comprises up to about 1 wt. % aromatics.

77. The process of claim 71 wherein the wash liquid effluent stream produced in (d) comprises at least about 1 wt. % of said at least one oxygenate.

78. The process of claim 71 wherein the wash liquid effluent stream produced in (d) comprises at least about 10 wt. % of said at least one oxygenate.

79. The process of claim 71 wherein the wash liquid effluent stream produced in (d) comprises at least about 20 wt. % of said at least one oxygenate.

80. The process of claim 71 wherein the wash liquid effluent stream produced in (d) comprises at least about 10 wt. % alcohol contained in the liquid alcohol-containing stream.

81. The process of claim 71 wherein the wash liquid effluent stream produced in (d) comprises at least about 20 wt. % alcohol contained in the liquid alcohol-containing stream.

82. The process of claim 71 further comprising exposing said wash liquid effluent stream produced in (d) to one or more reductions in pressure to form a wash flash liquid effluent stream, wherein said wash flash liquid effluent stream is provided as the portion of the wash liquid effluent stream for contacting (e).

83. The process of claim 82 wherein the wash flash liquid effluent stream comprises up to about 20 wt. % aromatics.

84. The process of claim 82 wherein the wash flash liquid effluent stream comprises at least about 20 wt. % alcohol contained in the liquid alcohol-containing stream.

85. The process of claim 82 wherein the wash flash liquid effluent stream comprises at least about 30 wt. % alcohol contained in the liquid alcohol-containing stream.

86. The process of claim 71 wherein the liquid water-containing stream in (e) comprises at least 90 wt. % water.

87. The process of claim 71 wherein the liquid water-containing stream in (e) comprises at least 95 wt. % water.

88. The process of claim 71 wherein said organic phase in (e) comprises up to about 95 wt. % $C_5+$ hydrocarbons.

89. The process of claim 71 wherein said organic phase in (e) comprises up to about 75 wt. % $C_5+$ hydrocarbons.

90. The process of claim 71 wherein said organic phase in (e) comprises up to about 40 wt. % $C_2$ to $C_6$ carbonyls.

91. The process of claim 71 wherein said organic phase in (e) comprises up to about 25 wt. % $C_2$ to $C_6$ carbonyls.

92. The process of claim 71 wherein said contacting (e) is conducted at a pressure of from about 170 kPaa (10 psig) to about 2514 kPaa (350 psig), and a temperature of from about 1° C. (34° F.) to about 54° C. (130° F.).

93. The process of claim 71 wherein said contacting (e) is conducted within said liquid-liquid contacting device at a pressure of from about 446 kPaa (50 psig) to about 1480 kPaa (200 psig), and a temperature of from about 21° C. (70° F.) to about 43° C. (110° F.).

94. The process of claim 71 further comprising fractionating the aqueous phase into a water-rich fraction and a fraction rich in said at least one oxygenate.

95. The process of claim 94 wherein at least a portion of said liquid water-containing stream in (e) is at least a portion of said water-rich fraction.

96. The process of claim 71 wherein said condensed liquid effluent stream and said wash liquid effluent stream, or portions thereof, are combined, and said combined stream, or portion thereof, is provided for contacting (e).

97. The process of claim 71 wherein said condensed liquid effluent stream and said wash liquid effluent stream, or portions thereof, are combined, and said combined stream, or portion thereof, is exposed to one or more reductions in pressure to form a flash liquid effluent stream, wherein said flash liquid effluent stream is provided as the portion of the wash liquid effluent stream for contacting (e).

98. The process of claim 71 wherein (c) comprises compressing the first vapor effluent stream; cooling the compressed first vapor effluent stream to produce a first condensed liquid effluent steam and a first residual vapor effluent stream; compressing the first residual vapor effluent stream; and cooling the compressed first residual vapor effluent stream to produce a second effluent stream that is at least partially in the vapor state, at least part of said second effluent stream being provided for said washing (d).

99. The process of claim 98 wherein said second effluent stream is segregated into a second condensed liquid effluent stream and a second residual vapor effluent stream, said second residual vapor effluent stream being provided for said washing (d).

100. The process of claim 99 wherein said first condensed liquid effluent stream, said second condensed liquid effluent stream or said wash liquid effluent steam, or portions thereof, is exposed to one or more reductions in pressure to form a flash liquid effluent stream, wherein said flash liquid effluent stream is provided as the portion of the condensed liquid effluent stream and wash liquid effluent stream for contacting (e).

101. The process of claim 99 wherein said second condensed liquid effluent stream and said wash liquid effluent stream, or portions thereof, are exposed to a reduction in pressure along with the compressed and cooled first vapor effluent stream to produce a first residual vapor effluent stream and a common first condensed liquid effluent stream and first flash liquid effluent stream, said common first condensed liquid effluent stream and first flash liquid effluent stream being exposed to a further reduction in pressure to produce a second flash liquid effluent stream, and said second flash liquid effluent stream being provided as the portion of the condensed liquid effluent stream and wash liquid effluent stream for contacting (e).

* * * * *